(12) United States Patent
Beger et al.

(10) Patent No.: US 8,021,424 B2
(45) Date of Patent: Sep. 20, 2011

(54) INTERVERTEBRAL IMPLANT

(75) Inventors: Jens Beger, Tuttlingen (DE); Cécile Wagner, Tuttlingen (DE); Alexander Haas, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 267 days.

(21) Appl. No.: 12/321,591

(22) Filed: Jan. 21, 2009

(65) Prior Publication Data

US 2009/0192614 A1 Jul. 30, 2009

(30) Foreign Application Priority Data

Jan. 25, 2008 (DE) .......................... 10 2008 005 998

(51) Int. Cl.
*A61F 2/44* (2006.01)
(52) U.S. Cl. ..................................................... 623/17.11
(58) Field of Classification Search ..... 623/17.11–17.16
See application file for complete search history.

(56) References Cited

U.S. PATENT DOCUMENTS

| | | | | |
|---|---|---|---|---|
| 4,349,921 A | * | 9/1982 | Kuntz | 623/17.16 |
| 4,834,757 A | * | 5/1989 | Brantigan | 623/17.11 |
| 5,314,478 A | | 5/1994 | Oka et al. | |
| 5,425,772 A | * | 6/1995 | Brantigan | 623/17.11 |
| 5,443,514 A | * | 8/1995 | Steffee | 128/898 |
| 5,458,643 A | | 10/1995 | Oka et al. | |
| 5,534,030 A | | 7/1996 | Navarro et al. | |
| 5,674,294 A | | 10/1997 | Bainville et al. | |
| 5,674,295 A | * | 10/1997 | Ray et al. | 623/17.12 |
| 5,824,094 A | | 10/1998 | Serhan et al. | |
| 6,110,210 A | * | 8/2000 | Norton et al. | 623/17.16 |
| 6,132,465 A | * | 10/2000 | Ray et al. | 623/17.16 |
| 6,139,579 A | | 10/2000 | Steffee et al. | |
| 6,162,252 A | | 12/2000 | Kuras et al. | |
| 6,258,125 B1 | * | 7/2001 | Paul et al. | 623/17.11 |
| 6,348,071 B1 | | 2/2002 | Steffee et al. | |
| 6,533,817 B1 | * | 3/2003 | Norton et al. | 623/17.16 |
| 6,669,732 B2 | | 12/2003 | Serhan et al. | |
| 6,699,288 B2 | * | 3/2004 | Moret | 623/17.16 |
| 6,764,514 B1 | * | 7/2004 | Li et al. | 623/17.12 |
| 6,942,697 B2 | * | 9/2005 | Lange et al. | 623/17.11 |
| 7,083,650 B2 | * | 8/2006 | Moskowitz et al. | 623/17.11 |
| 7,169,183 B2 | * | 1/2007 | Liu et al. | 623/17.16 |
| 7,288,114 B2 | * | 10/2007 | Lange | 623/17.11 |
| 7,591,853 B2 | * | 9/2009 | Felt et al. | 623/17.16 |
| 2001/0016773 A1 | | 8/2001 | Serhan et al. | |
| 2002/0022888 A1 | | 2/2002 | Serhan et al. | |

(Continued)

FOREIGN PATENT DOCUMENTS

DE 698 14 460 3/2004

(Continued)

*Primary Examiner* — Eduardo C Robert
*Assistant Examiner* — Mary Hoffman
(74) *Attorney, Agent, or Firm* — Lipsitz & McAllister, LLC

(57) ABSTRACT

In order, in an intervertebral implant having a core made of a swellable material and having a vertebral-body locating face on its top and/or bottom side, which is connected to the swellable core, to reduce the shearing forces between the swellable core and the vertebral-body locating face during swelling of the swellable core, it is proposed that the vertebral-body locating face comprises a plurality of support elements, which are respectively anchored adjacent to one another and individually in the core, and a plurality of mutually separate locating elements, which are disposed adjacent to one another and outside of the core and which are carried by the support elements and are movable relative to one another in the plane of the vertebral-body locating face.

24 Claims, 21 Drawing Sheets

U.S. PATENT DOCUMENTS

| | | |
|---|---|---|
| 2003/0100951 A1 | 5/2003 | Serhan et al. |
| 2004/0054411 A1* | 3/2004 | Kelly et al. ............... 623/17.13 |
| 2004/0068320 A1 | 4/2004 | Robie et al. |
| 2004/0249464 A1 | 12/2004 | Bindseil et al. |
| 2005/0060036 A1 | 3/2005 | Schultz et al. |
| 2005/0143822 A1* | 6/2005 | Paul ........................ 623/17.16 |
| 2005/0209696 A1 | 9/2005 | Lin et al. |
| 2005/0216087 A1 | 9/2005 | Zucherman et al. |
| 2006/0058881 A1 | 3/2006 | Trieu |
| 2006/0173542 A1 | 8/2006 | Shikinami |
| 2006/0265075 A1 | 11/2006 | Baumgartner et al. |
| 2007/0016302 A1 | 1/2007 | Dickman |
| 2007/0150059 A1 | 6/2007 | Ruberte et al. |
| 2007/0239277 A1 | 10/2007 | Beger et al. |
| 2007/0260324 A1 | 11/2007 | Joshi et al. |
| 2007/0270969 A1 | 11/2007 | Schmid |
| 2008/0177392 A1* | 7/2008 | Williams et al. ........... 623/17.16 |
| 2008/0306609 A1 | 12/2008 | Lee et al. |

FOREIGN PATENT DOCUMENTS

| | | |
|---|---|---|
| DE | 698 20 467 | 10/2004 |
| DE | 103 33 659 | 12/2004 |
| DE | 20 2006 005 896 | 6/2006 |
| DE | 698 32 812 | 8/2006 |
| EP | 0 317 972 | 5/1989 |
| EP | 0 392 076 | 10/1990 |
| EP | 0 610 837 | 8/1994 |
| EP | 1 173 120 | 10/2005 |
| WO | 2004/089257 | 10/2004 |
| WO | 2006/078662 | 7/2006 |

\* cited by examiner

INTERVERTEBRAL IMPLANT

The present disclosure relates to the subject matter disclosed in German patent application 10 2008 005 998.6 of Jan. 25, 2008, which is incorporated herein by reference in its entirety and for all purposes.

BACKGROUND OF THE INVENTION

The invention relates to an intervertebral implant having a core made of a swellable material and having a vertebral-body locating face on its top and/or bottom side, which is connected to the swellable core.

Such an intervertebral implant is described for example in DE 20 2006 005 896 U1. Such an intervertebral implant comprises two end plates made of metal or plastics material, between which is disposed a hydrogel core that is made of a swellable material, which by absorbing water may increase its volume and hence bear a specific structural similarity to a natural intervertebral disk. In order to connect the swellable core to an integral, rigid end plate, in the known intervertebral implant the end plate is provided with thread- or rod-shaped anchoring portions, which extend at a spacing from the end plate and project into the core of swellable material.

Since in the known design a rigid end plate is used, the different expansion behaviour of the end plate made of metal or plastics material, on the one hand, and the swellable core, on the other hand, leads to the production of high shearing forces during the swelling of the swellable material. Such an intervertebral implant moreover has a relatively large cross section because this cross section is determined i.a. by the extent of the end plate.

The object of the invention is to provide an intervertebral implant of the described type in a way that avoids the occurrence of high shearing forces between the vertebral-body locating face, on the one hand, and the swellable core, on the other hand, and moreover facilitates the insertion of the intervertebral implant through a narrow body opening.

SUMMARY OF THE INVENTION

In an intervertebral implant of the type described in the introduction this object is achieved according to the invention in that the vertebral-body locating face comprises a plurality of support elements, which are anchored respectively adjacent to one another and individually in the core, and a plurality of mutually separate locating elements, which are disposed adjacent to one another and outside of the core and which are carried by the support elements and are movable relative to one another in the plane of the vertebral-body locating face.

With the disclosed construction of an intervertebral implant, therefore, the vertebral-body locating face is broken up into individual, mutually adjacent locating elements that may move relative to one another in the plane of the vertebral-body locating face. These locating elements are supported by means of support elements in the core, so that during swelling of the core and during its expansion in a direction parallel to the plane of the vertebral-body locating face such an expansion is in no way impeded by the locating elements because these locating elements are able to move freely independently of one another in the plane of the vertebral-body locating face and therefore do not lead to any obstruction of the expansion of the core as a result of the swelling operation.

In a preferred embodiment of the invention, in each case a support element and a locating element are permanently connected to one another, in particular a support element and a locating element may be constructed integrally with one another. Given such an arrangement, it is clearly evident that during the swelling of the core and the variation of the dimension of the core in the plane of the vertebral-body locating face the individual locating- and support elements are simply moved only laterally, i.e. the mutual spacing of the locating elements is increased but no increased shearing forces are introduced into the core.

By virtue of the arrangement of the vertebral-body locating face, the intervertebral implant in the non-swollen state of the core, i.e. during introduction into the body, has a particularly small cross section because the individual locating elements are as close as possible to one another and it is only during swelling of the swellable material in the body that the locating elements move apart from one another and then cover the entire vertebral-body locating face, by means of which the support on the adjacent vertebral body is effected. The cross-sectional area taken up by the locating elements during introduction is therefore smaller than the cross-sectional area of the vertebral-body locating face after swelling occurs.

In a first preferred embodiment, the support elements are spheres, which are partially embedded in the core and of which the part projecting from the core forms in each case a locating element. These spheres may be distributed uniformly over the cross-sectional area of the core and hence form a plurality of support points, against which the adjacent vertebral body is supported.

In another embodiment, it may be provided that the support element comprises a foot, which engages into the core and has a widened portion, in particular the widened portion may have the shape of a sphere. In this way the support element is securely anchored in the core, the widened portion forming an undercut that ensures that the support element is supported in the core and is therefore capable of transferring a load, the foot moreover also being locked against rotation because it projects partially into the material of the expandable core.

It is advantageous if the locating element is of a plate-shaped configuration.

In this case, in particular all of the locating elements may lie in one plane.

In a first preferred embodiment it is provided that the locating elements in the non-swollen state of the core lie adjacent to one another without an overlap. During insertion into the body the locating elements therefore form a closed locating face, which after introduction is then pulled apart into individual regions as a result of the swelling of the swellable material.

In another preferred embodiment it is provided that the locating elements in the non-swollen state of the core lie adjacent to one another so as to mutually overlap in an edge region. In particular, the locating elements may be bevelled in the edge region of mutual overlap in the non-swollen state of the core. The effect achievable thereby is that, even when the core has expanded and the locating elements have moved apart from one another, only a small gap or no gap at all arises between the locating elements, i.e. support over substantially the entire surface area is possible.

The individual support elements and/or locating elements may be movable totally independently of adjacent support elements and/or locating elements. In a particularly preferred embodiment it is however provided that mutually adjacent support elements and/or locating elements are connected to one another by means of a limiting element, which during the expansion of the core allows but limits a moving of the support elements and/or locating elements apart from one another. Such a limiting element may for example be of an annular configuration and surround in each case two mutually adjacent support elements and/or locating elements. The limiting element then practically forms a chain link between the adjacent support elements and/or locating elements, which in the non-swollen state of the core loosely surrounds the two parts but during the swelling and during the moving-apart of the parts comes into abutment with these parts and then upon attainment of a specific maximum spacing prevents any further movement apart.

In a preferred embodiment, the support element and/or the locating element has an eye-shaped portion, through which the limiting element engages.

It is advantageous if all of the mutually adjacent support elements and/or locating elements in a row are connected to one another by limiting elements. In this way, the extent of the vertebral-body locating face is limited to a maximum value in one dimension but not transversely thereto.

It is however also possible for support elements and/or locating elements from mutually adjacent rows to be additionally connected to one another by limiting elements. This leads to a limiting of the moving-apart in two directions, which extend at right angles to one another and which both lie in the plane of the vertebral-body locating face.

It may be provided that the support elements and the locating elements at their sides facing one another are of an eye-shaped configuration and engage around one another in this eye-shaped region. In this case, locating elements and support elements are therefore connected to one another, not rigidly, but so as to be displaceable relative to one another, wherein the displacement movement is limited by the engagement of the eye-shaped regions with one another.

In other embodiments, the support elements and the locating elements at their sides facing one another are of an eye-shaped configuration, and are connected to one another in this eye-shaped region by limiting elements so as to be movable up to a maximum spacing apart from one another.

The eye-shaped regions are preferably of a circular configuration, with it however also being possible in a modified embodiment to design the eye-shaped regions in such a way that they are formed by the lateral faces of a three-dimensional body composed of rod-shaped edge elements, with it being possible in particular for this three-dimensional body to be a cuboid and in particular a cube.

In a further preferred embodiment, it is provided that there are disposed between the locating elements fixing projections, which are displaceable transversely of the plane of the vertebral-body locating face and which are displaceable from a normal position, in which they do not project beyond the locating elements, into a fixing position, in which they project beyond the locating elements, and that for displacement of the fixing projections drive elements are provided, which can be activated by the movement of the support elements and/or the locating elements apart from one another during the swelling of the core. The displacement of the support elements and/or of the locating elements that occurs because of the increase of the volume of the core during swelling is therefore utilized and this displacement movement is simultaneously used to displace the fixing projections transversely of the vertebral-body locating face. As a result, the fixing projections protrude from the vertebral-body locating face and penetrate into the adjacent vertebra.

It may for example be provided that the drive element comprises diverging locating faces for tension members, which are held in each case on a support element and/or locating element and, when the support elements and/or locating elements move apart from one another, slide along the locating faces in such a way that the drive element is displaced in the direction of the vertebral-body locating face.

In particular, the locating faces may be formed by the limbs of a triangular drive element.

Such a drive element may moreover take the form of a limiting element that allows adjacent support elements and/or locating elements to move up to a maximum spacing apart from one another, i.e. the function of the drive element for a fixing projection and the function of the limiting element may be combined in one component, which limits the movement of adjacent, support elements and/or locating elements apart from one another.

The following description of preferred embodiments of the invention serves in connection with the drawings to provide a detailed explanation.

DETAILED DESCRIPTION OF THE INVENTION

Figure 1:
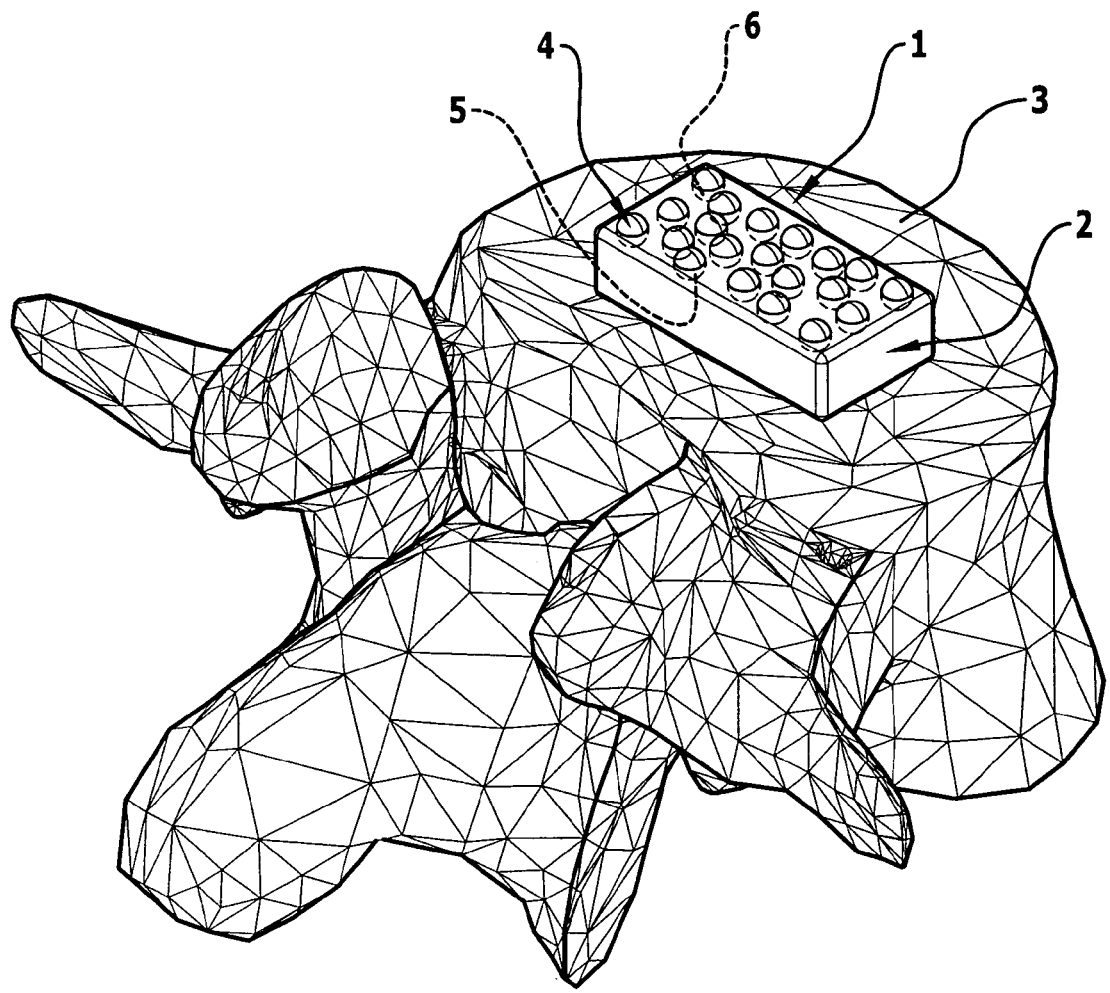
FIG. 1: is a perspective view of a vertebral body implant with a swellable core and with support- and locating elements in the form of spheres embedded therein.

The intervertebral implant 1 represented in the drawings has as a principal part a core 2 made of a swellable material. In the embodiments represented in the drawings the core is in the shape of a cuboid, with other shapes also being usable, wherein the core 2 will as a rule be of a plate-shaped design with a flat top and a flat underside, although the external contour might alternatively be adapted to the external contour of a vertebral body 3.

The principal feature of the swellable material is that the volume of the swellable material in the dehydrated state, i.e. without a large liquid content, is small and increases considerably upon the absorption of liquid, in particular water. Thus, the core 2 expands when it is introduced into the body.

As swellable materials so-called hydrogels may be used. In this case, these may be in principle any non-degradable hydrophilic polymers, for example polyacrylic acid and its derivates such as polymethacrylic acid, polyacrylamide, polyacrylonitrile, polyacrylate, polyhydroxy ethylmethacrylates, polyvinyl pyrrolidone (PVP), polyurethanes, high-molecular weight polyvinyl alcohol.

Also conceivable are polymer blends (copolymers that are connected to one another by chemical bonds) of the above-mentioned polymers or interpenetrating networks (IPNS) of the above-mentioned polymers. IPNs consist of at least two different polymers, the polymer chains of which are interlocked and are connected to one another by physical interactions (van der Waals, electrostatic, hydrogen bridge bonds and/or ionic forces).

Further polymer blends that may be used are copolymers as well as IPNs of polyacrylates (polyacrylic acid and its derivatives such as polymethacrylic acid, polyacrylamide, polyacrylonitrile, polyacrylate) with polycaprolactone.

Figure 2:
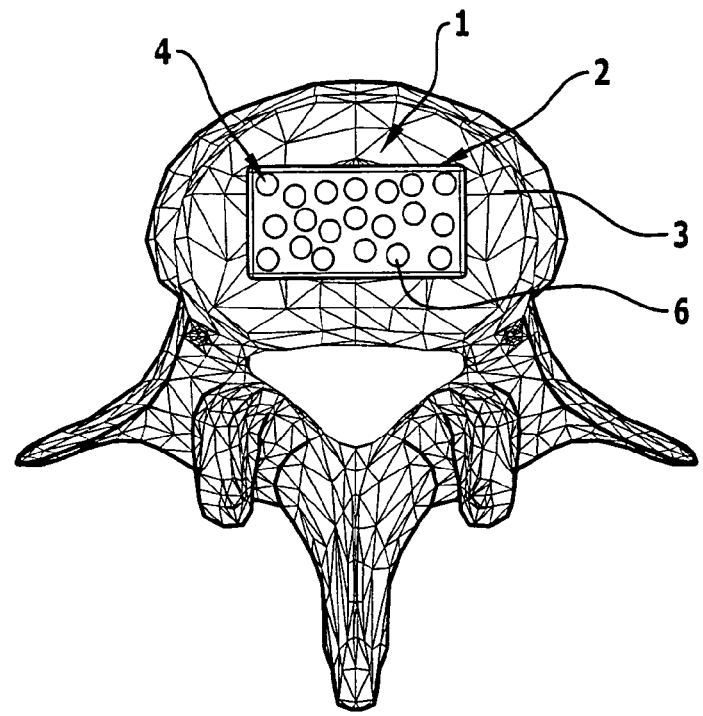
FIG. 2: is a plan view of a vertebral body with an intervertebral implant according to FIG. 1 prior to swelling of the core.
Figure 3:
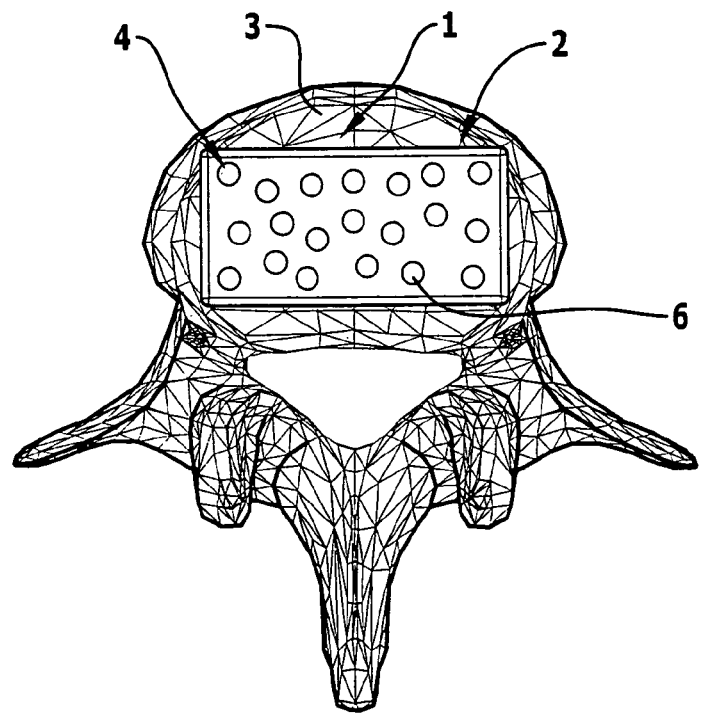
FIG. 3: is a view similar to FIG. 2 after swelling of the core.
Figure 4:
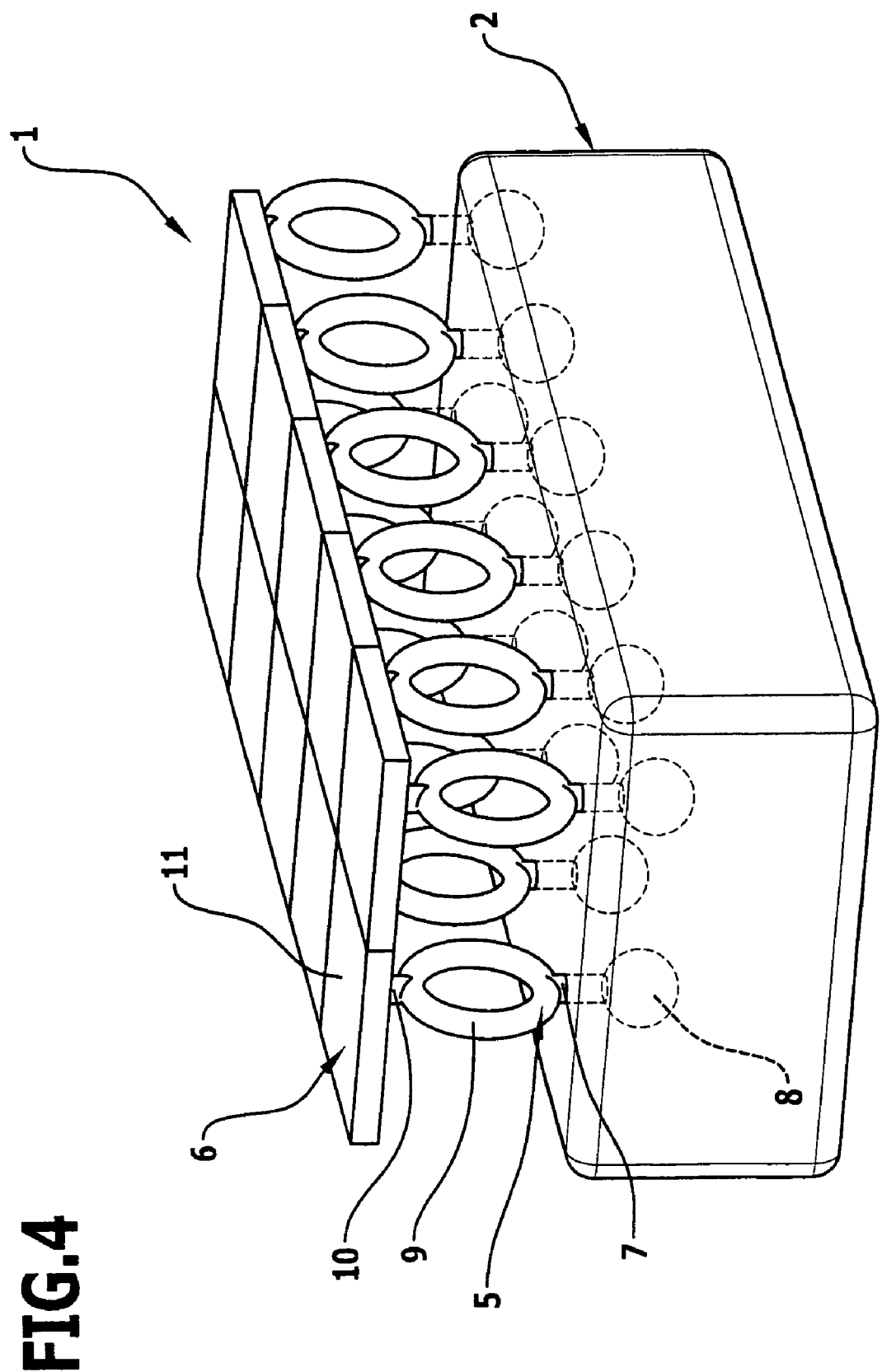
FIG. 4: is a perspective view of a further preferred embodiment of an intervertebral implant with a core made of a swellable material and with integral support- and locating elements embedded therein, which are movable apart from one another independently of one another.
Figure 5:
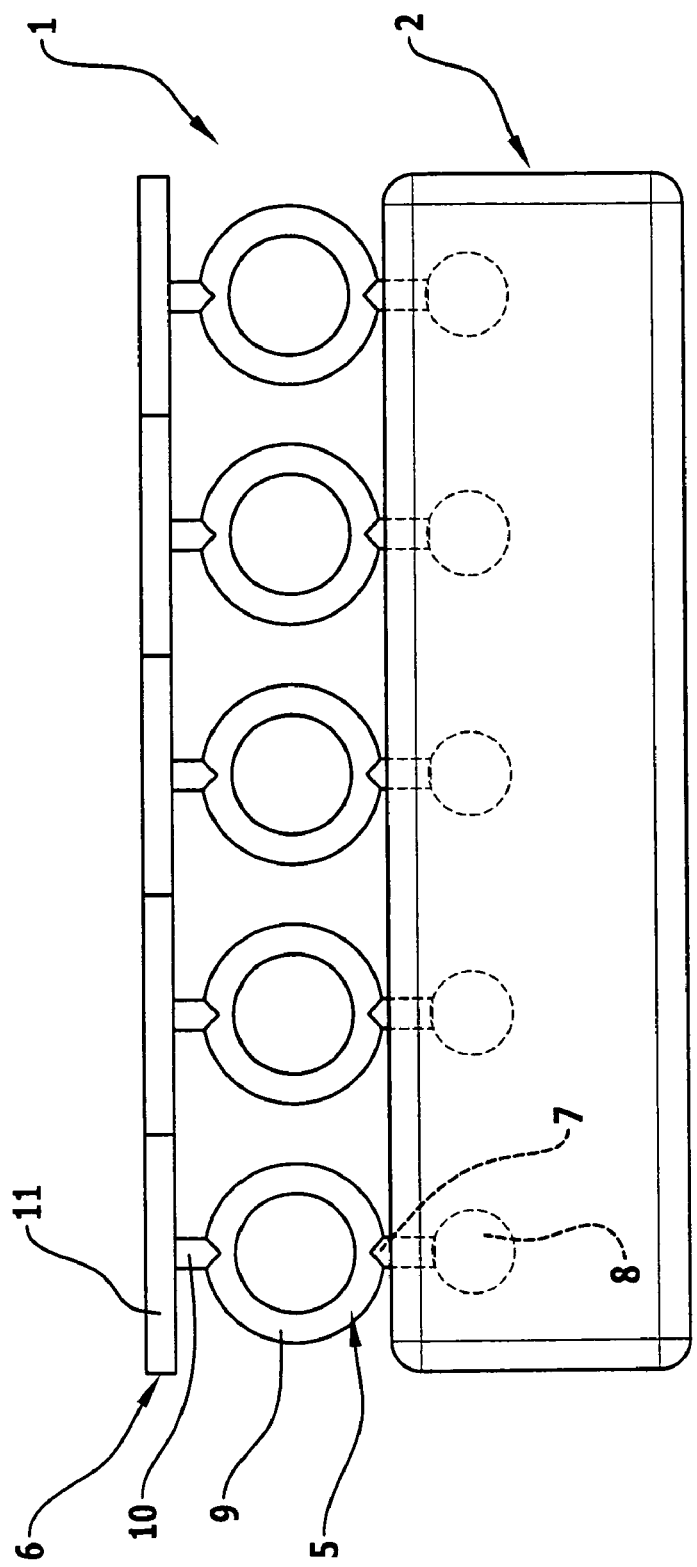
FIG. 5: is a side view of the intervertebral implant of FIG. 4.
Figure 6:
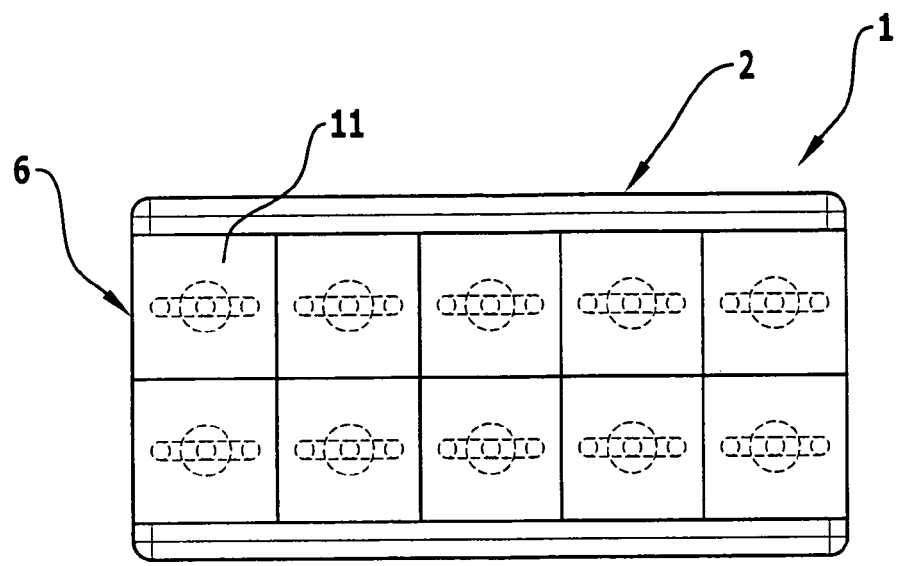
FIG. 6: is a diagrammatic plan view of the intervertebral implant of FIG. 4 prior to swelling of the core.

In the embodiment of FIGS. 1 to 3, a plurality of spheres 4 are embedded in the upper side of the plate-shaped or cuboidal core, namely in such a way that the greater part extends into the material of the core 2, while a smaller part projects upwards from the core 2. The drawings show such spheres 4 only at the top of the core 2 but it is easily possible for the intervertebral implant 1 to be of an identical design at the opposite, bottom side. This applies both to the intervertebral implant of FIGS. 1 to 3 and to all of the other embodiments that are discussed below, for which in each case only the configuration at one side of the core 2 is shown and discussed in detail. At the opposite side too, the intervertebral implants 1 may be configured in the same way as is shown and described for the upper side of the intervertebral implant 1.

In the embodiment of FIGS. 1 to 3, the spheres 4 with their parts embedded in the core 2 form in each case a support element 5, by which the spheres 4 are supported in the core 2, while the regions of the spheres 4 that project from the core 2 form locating elements 6, which are positioned against and therefore support the adjacent vertebral body.

In the embodiment of FIGS. 1 to 3 the spheres 4 are practically both a supporting element 5 and a locating element 6, i.e. both functions coincide in one component.

In the dehydrated state, the core 2 has a low volume and hence also a small cross-sectional area, as is evident from the representation of FIG. 2. After being introduced into the body and after absorbing liquid from the area surrounding the site of the operation, the material of the core 2 swells and so the cross section of the core 2 also increases, in the manner illustrated in FIG. 3. Simultaneously with the increase of the cross-sectional area of the core 2, the spheres 4 are moved apart from one another, i.e. their mutual spacing increases. In this way, after swelling of the core 2 the spheres 4 are also distributed substantially uniformly over the entire cross-sectional area of the core 2 and, there, form support points for supporting the adjacent vertebral body.

This principle is realized also in the embodiment of an intervertebral implant such as is shown in FIGS. 4 to 7. In this embodiment, rod-shaped feet 7 are embedded in the core 2 at right angles to the upper side thereof and carry on their free end a spherically widened portion 8. The feet 7 project slightly from the core 2 and form there an annular and eye-shaped portion 9, from which at the opposite end to the foot 7 a connecting rod 10 protrudes and runs into the underside of a locating plate 11. In the embodiment shown in FIGS. 4 to 7 the locating plates 11 have the shape of a cuboid, the locating plates 11 in the non-swollen state of the core 2 lying close together, without forming a gap, in a single plane extending parallel to the upper side of the core 2, the locating plates 11 jointly forming a vertebral-body locating face.

The foot 7 with the widened portion 8, the eye-shaped portion 9 and the connecting rod 10 correspond to the support element 5 in the embodiment of FIGS. 1 to 3, while the locating plates 11 correspond to the locating element 6.

Figure 7:
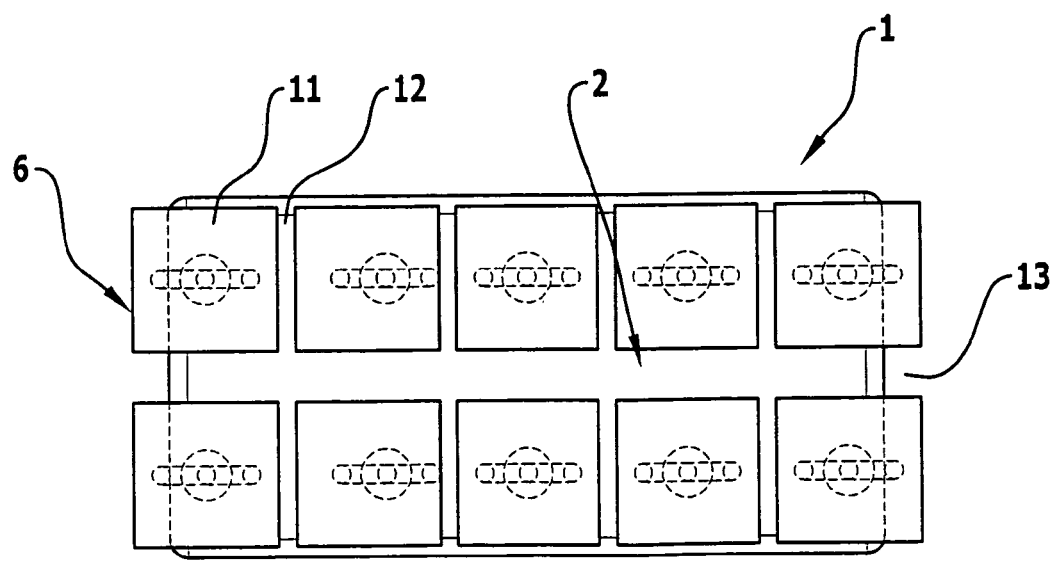
FIG. 7: is a view similar to FIG. 6 after swelling of the core.

When the material of the core 2 absorbs liquid and swells, the core 2 expands laterally so that it occupies a larger area. In this case, the support elements 5 embedded in the core 2 and connected to the locating elements 6 are moved apart from one another, thereby producing gaps 12, 13 between the individual locating plates 11 (FIG. 7). As a whole, the vertebral-body locating face is therefore enlarged without high shearing forces simultaneously being exerted on the core 2, as is the case with integral known locating elements. The vertebral-body locating face in this case comprises individual elements, which are disposed adjacent to one another like scales and which during the swelling of the core 2 easily follow the movement of the core material and move apart from one another in accordance with the increase in the volume of the core 2.

Figure 8:
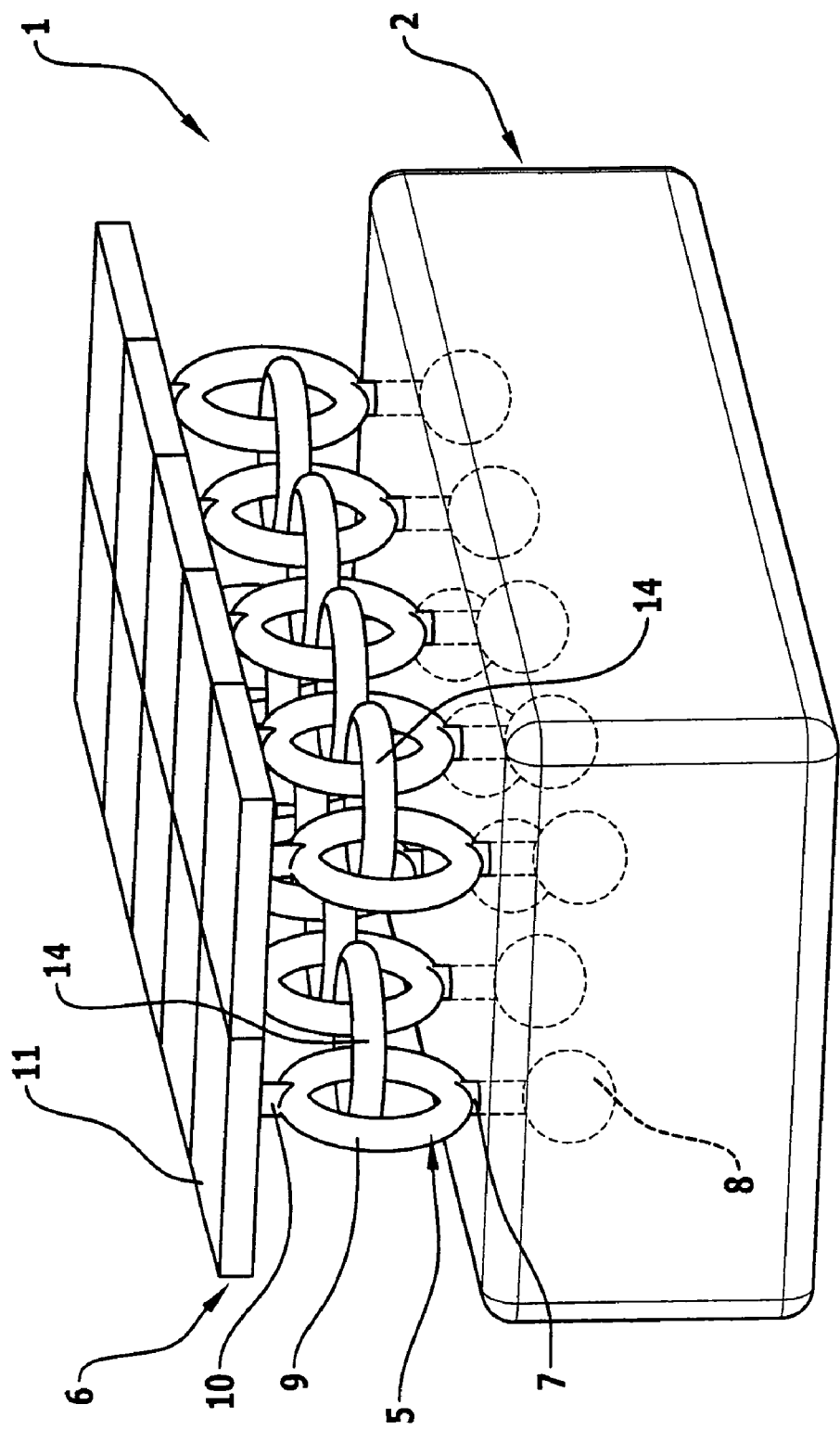
FIG. 8: is a view of a further preferred embodiment of a intervertebral implant similar to that of FIG. 4 with limiting elements that limit the moving-apart of the support- and locating elements of in each case one row.
Figure 9:
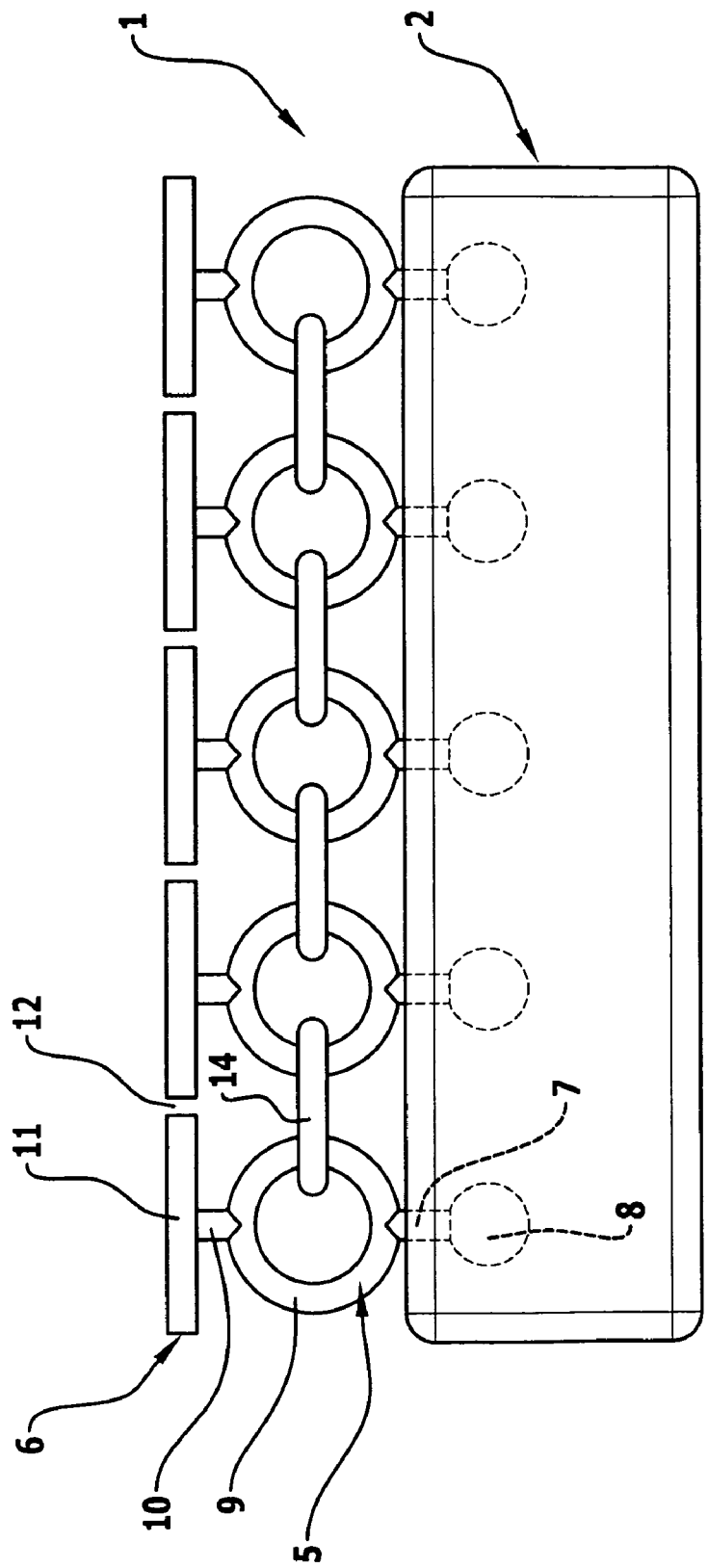
FIG. 9: is a side view of the intervertebral implant of FIG. 9.

Since in the embodiment of FIGS. 8 and 9 a similar structure to that of the intervertebral implant of FIGS. 4 to 7 is selected, parts that correspond to one another bear the same reference characters. In addition to the constructional features of the intervertebral implant of FIGS. 4 to 7, in the embodiment of FIGS. 8 and 9 each two mutually adjacent support elements 5 in a row are connected to one another by an annular limiting element 14, which engages through the eye-shaped portions 9 of two mutually adjacent support elements 5 in a row. When the core 2 prior to swelling has a small cross section, the limiting elements 14 are mounted loosely in the eye-shaped portion 9 but, when the support elements 5 move apart from one another as a result of the liquid absorption of the core 2, the limiting elements 14 are positioned tightly on the eye-shaped portions 9 and limit their movement apart from one another, i.e. during the swelling of the core 2 the gaps 12 between mutually adjacent locating plates 11 in a row reach a maximum width that is not exceeded (FIG. 9). From the representation of FIG. 9 it is also evident that the eye-shaped portions 9 and the annular limiting elements 14 as a whole form a construction similar to a chain, wherein the eye-shaped portions 9 on the one hand and the annular limiting elements 14 on the other hand act as chain links. The overall effect is to limit the moving-apart of the support elements 5 disposed in a row, while in the embodiment of FIGS. 8 and 9 no such limiting of the moving-apart occurs transversely thereof.

Figure 10:
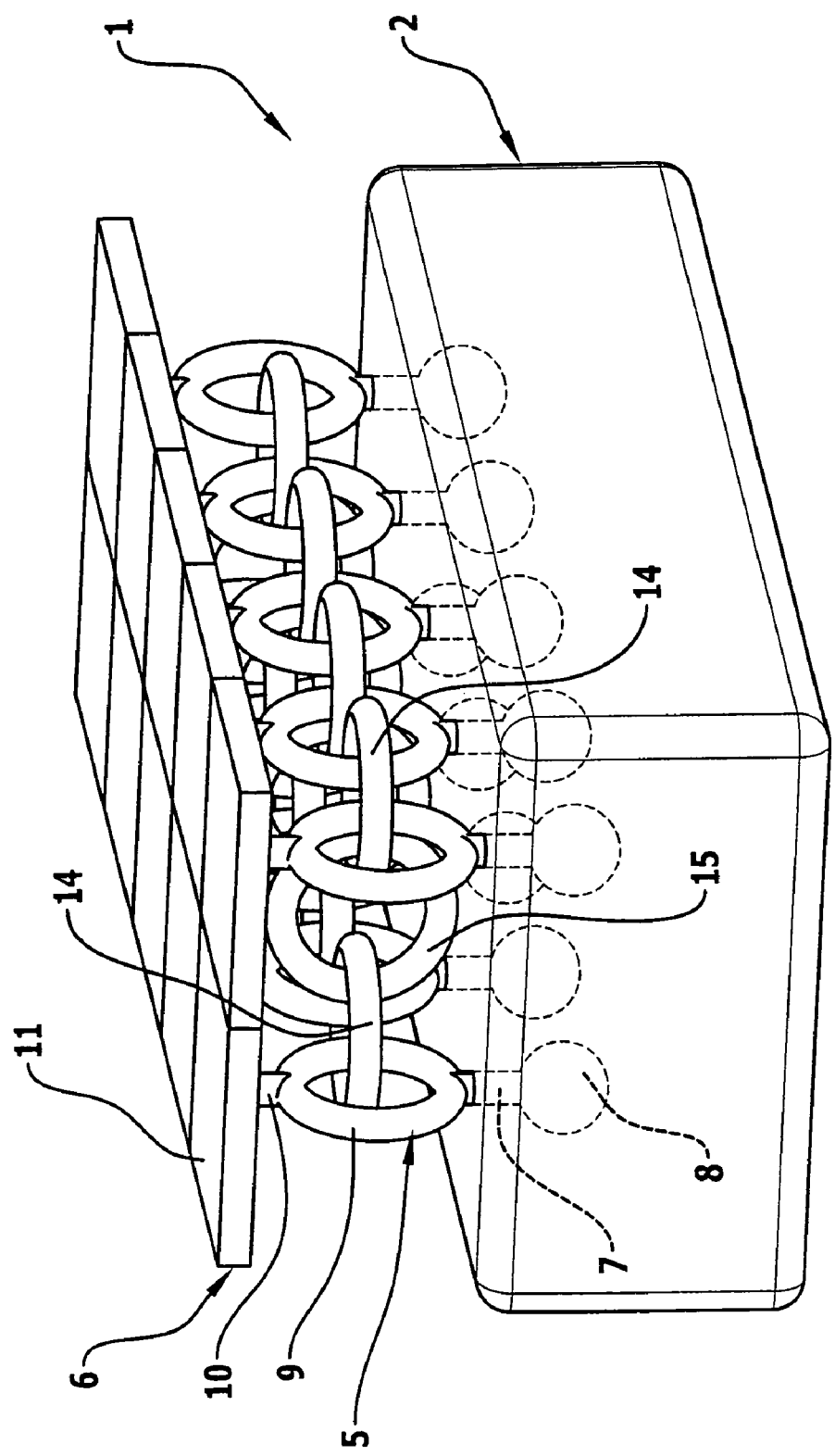
FIG. 10: is a perspective view of a further preferred embodiment of an intervertebral implant similar to FIG. 8 with additional limiting elements for limiting the moving-apart of the support- and locating elements in adjacent rows.
Figure 11:
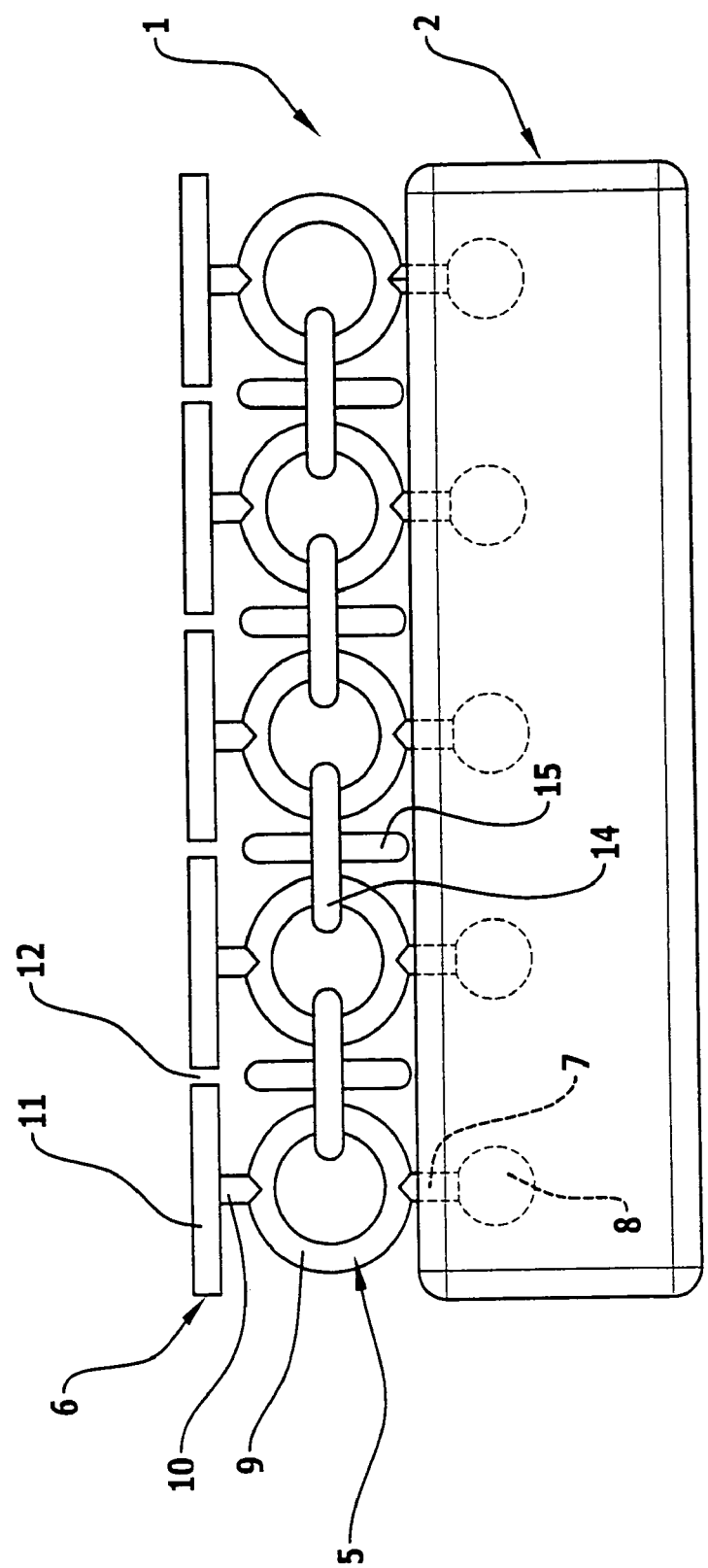
FIG. 11: is a side view of the intervertebral implant of FIG. 10.

Such an additional limiting of the expansion of the support elements 5 from adjacent rows is however achieved in the embodiment of FIGS. 10 and 11, which is of a substantially similar construction to the embodiment of FIGS. 8 and 9. In this case, however, additional limiting elements 15 are provided, which engage through the limiting elements 14 of the mutually adjacent support elements 5 of parallel, mutually adjacent rows of support elements 5. The result is a two-dimensional interlinking of the eye-shaped portions 9 of all of the support elements 5, the limiting elements 14 and 15 in this case being disposed in a plane between the core 2, on the one hand, and the locating plates 11, on the other hand. In this way, the increase of the spacing of the support elements 5 and hence of the locating elements 6 within a row and transversely thereof between adjacent rows is limited.

In the embodiments of FIGS. 4 to 10 the support elements 5 and the locating elements 6 are combined in one component. In contrast to this, in the embodiment of FIGS. 12 and 13 the support elements 5 and the locating elements 6 are separate components. The support elements 5 in their construction fully correspond to the support elements 5 of the embodiment of FIGS. 4 to 11, except that the connecting rod 10 opposite the foot 7 is absent in this case. The support elements 5 terminate at their upper side, i.e. at their side remote from the core 2, in the eye-shaped portion 9.

The locating plates 11 carry on their underside, i.e. on their side facing the core 2, a short connecting rod 16 that merges into a circular, eye-shaped portion 17. The eye-shaped portions 9 and 17 of the support element 5 on the one hand and of the locating element 6 on the other hand engage through one another, so that the spacing of the locating plates 11 from the core 2 is also variable.

Both the eye-shaped portions 17 and the eye-shaped portions 9 are connected to one another within a row and transversely thereof by means of annular limiting elements 14 and 15 and by means of these annular limiting elements 14, 15 upon an increase in the volume of the core 2 the expansion of the core 2 is limited in directions lying at right angles to one another.

Figure 12:
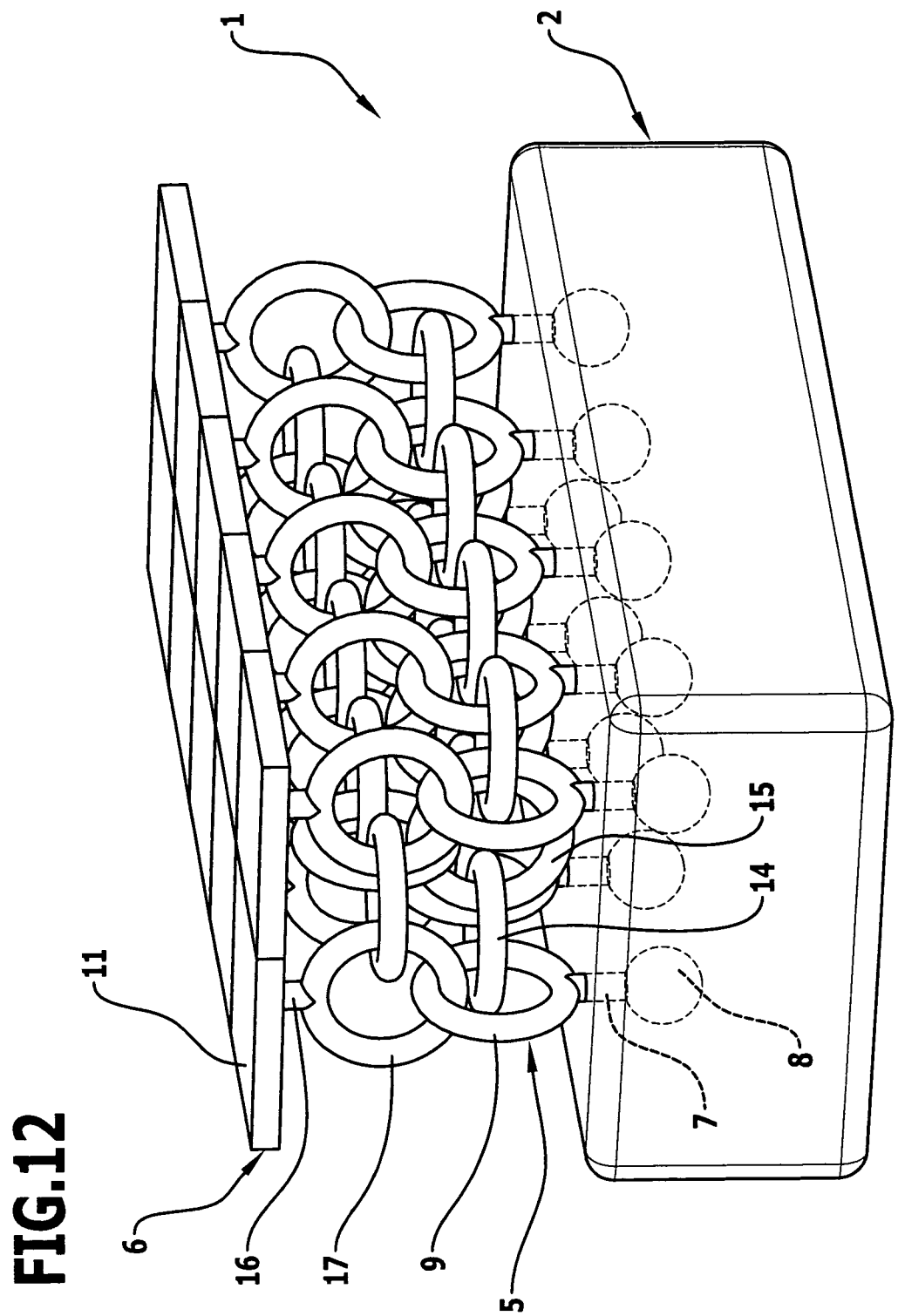
FIG. 12: is a perspective view of a further preferred embodiment of an intervertebral implant with a swellable core having support elements embedded therein as well as locating elements, which are coupled to the support elements by eye-shaped connections.
Figure 13:
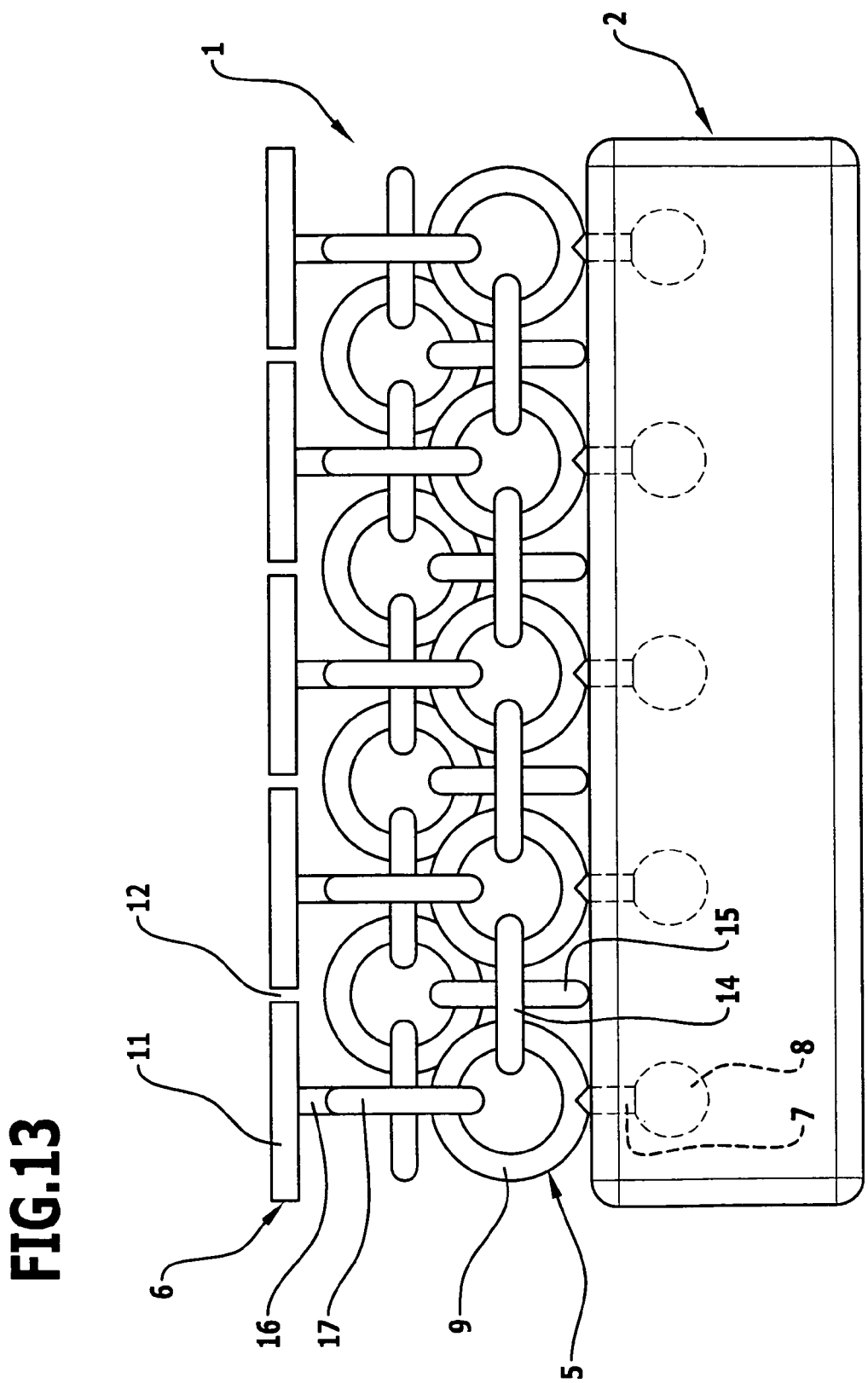
FIG. 13: is a side view of the intervertebral implant of FIG. 12.

In the construction of FIGS. 12 and 13, between the locating plates 11 on the one hand and the core 2 on the other hand two layers of two-dimensional chain surfaces are therefore situated one above the other, i.e. surfaces, the individual elements of which are connected to one another in a chain-like manner in two directions extending at right angles to one another.

Figure 14:
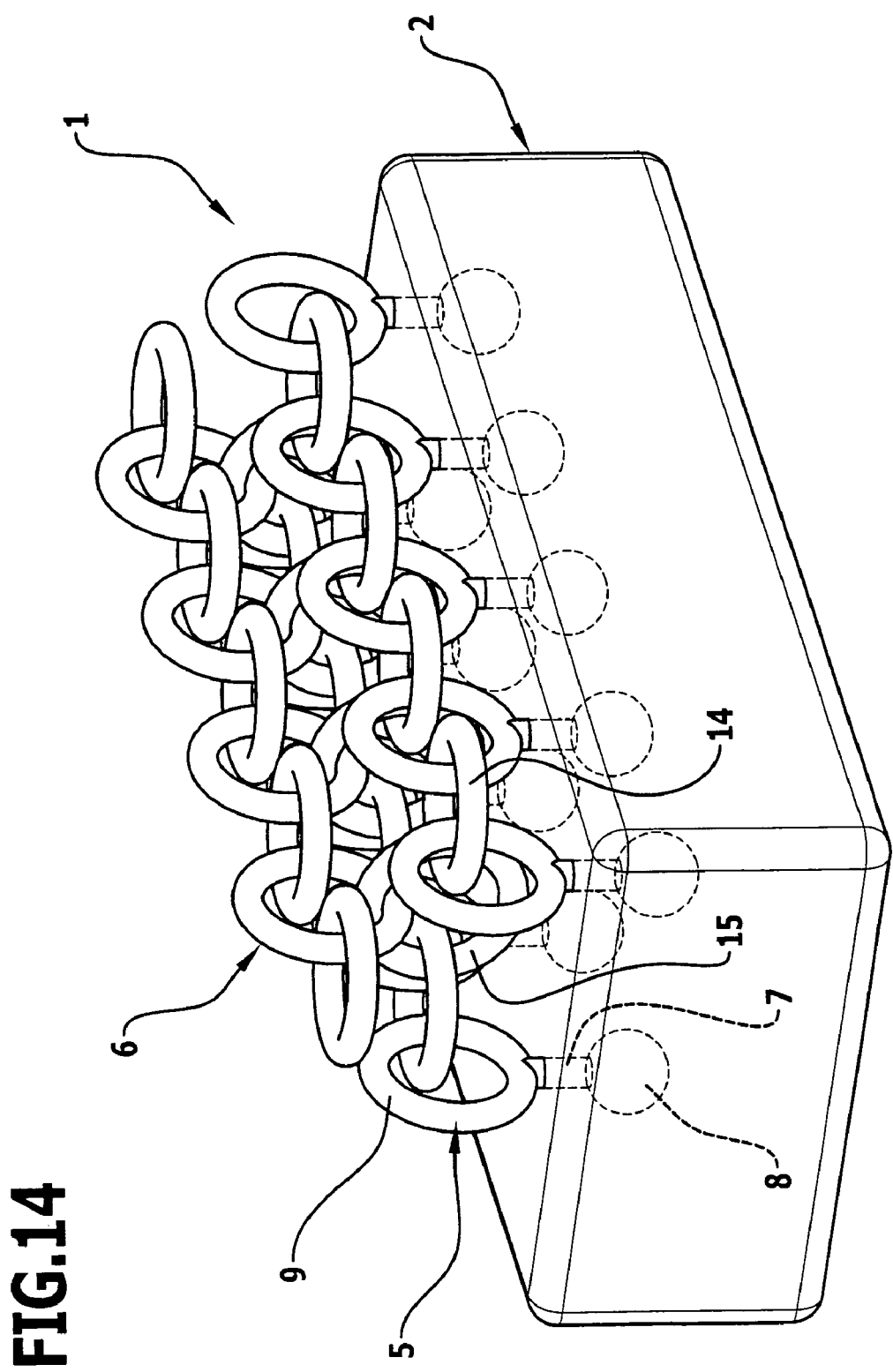
FIG. 14: is a perspective view of a further preferred embodiment of an intervertebral implant with annular or eye-shaped locating elements.
Figure 15:
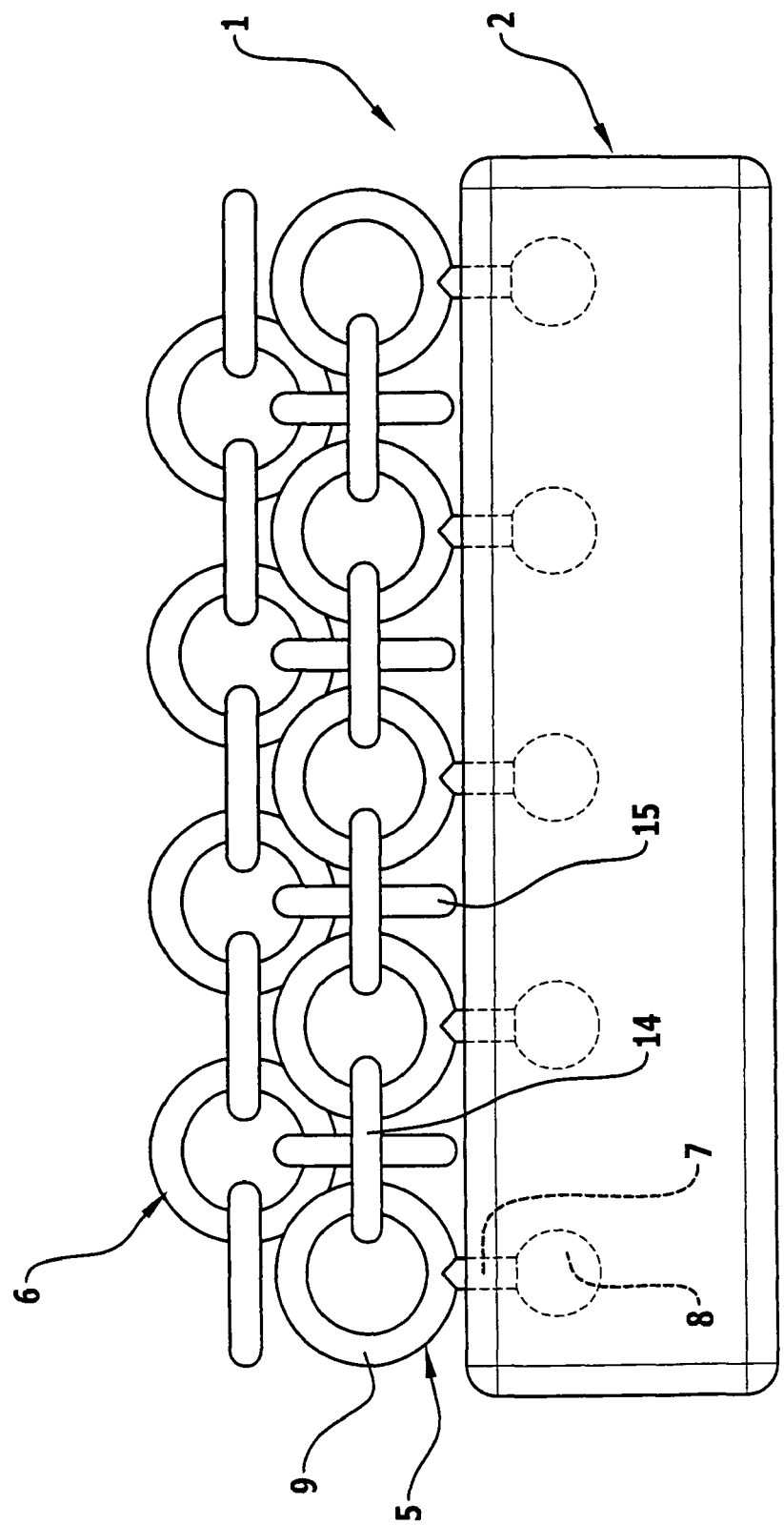
FIG. 15: is a side view of the intervertebral implant of FIG. 14.

In the embodiment of FIGS. 14 and 15 a similar construction to that of the embodiments of FIGS. 12 and 13 is selected, except that the locating plates 11 with the connecting rod 16 and the eye-shaped portions 17 have been omitted. This leaves only the limiting elements 14 and 15 of the upper layer of the chain surface, wherein these limiting elements 14 and 15 are disposed in the manner of a chain in the space between two adjacent rows of support elements 5 above these rows. The limiting elements 14 of this upper plane with their outer sides remote from the core 2 then form the locating elements 6, i.e. they rest against an adjacent vertebral body.

During the expansion of the core 2 the individual links of this chain are spread, with the result that the locating points are moved apart from one another, this expansion however being limited by the remaining limiting elements.

Figure 16:
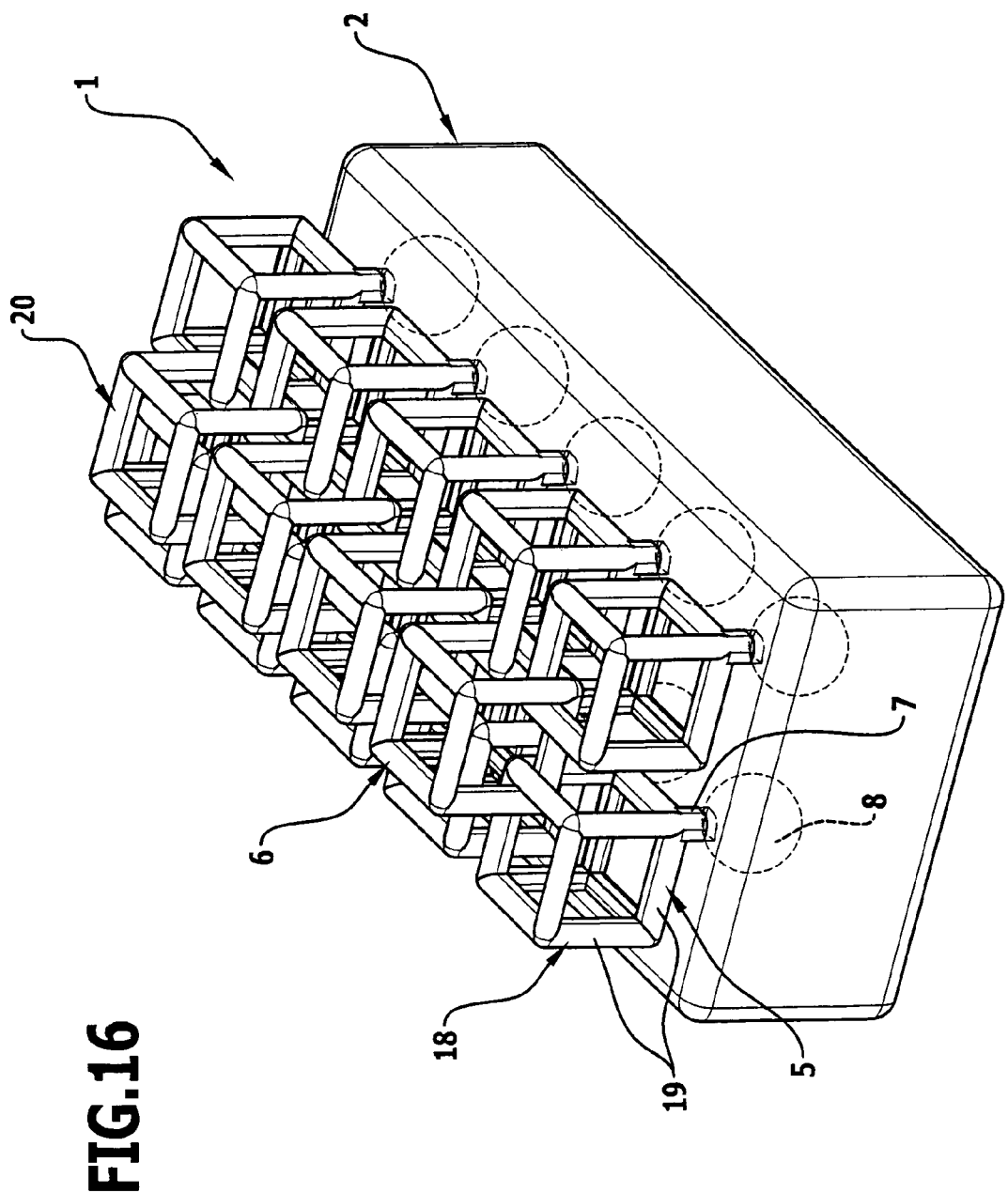
FIG. 16: is a perspective view of a further preferred embodiment of an intervertebral implant with cube-shaped support elements and cube-shaped locating elements.

In the embodiment of FIGS. 14 and 15 the chain links of the chain surfaces are of a circular shape. In contrast to this, in the embodiment of FIGS. 16 and 17 there are disposed on each foot 7 of a support element 5 cube-shaped support bodies 18, which each consist of rods 19 running along the edges of a cube, wherein the lateral faces are open. On one of the rods the foot 7 is disposed as an extension of the rod, and the support bodies 18 are disposed adjacent to one another in a plurality of parallel rows. A likewise cube-shaped locating body 20 engages in each case through four support bodies 18, wherein each of the vertical rods of the locating body 20 penetrates an open upper lateral face of one of four support bodies 18. This produces between two rows of cube-shaped support bodies 18 a row of cube-shaped locating bodies 20 that are at a greater distance from the core 2 than the support bodies 18.

Figure 17:
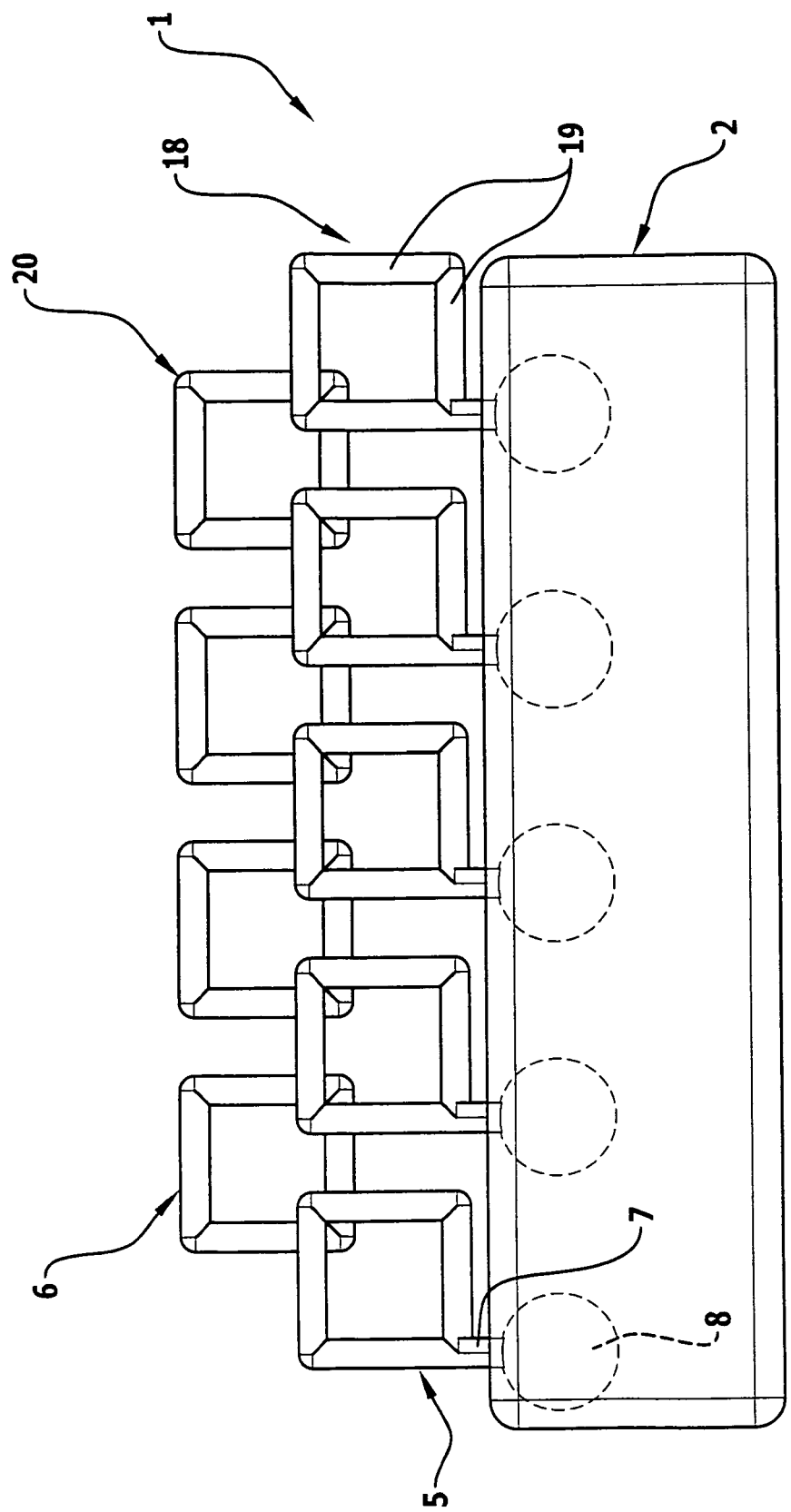
FIG. 17: is a side view of the intervertebral implant of FIG. 16.

During swelling of the core 2 the support bodies 18 may move apart from one another in two directions lying at right angles to one another, this expansion being limited by the abutment of the edges of the locating body 20 with the edges of the support bodies 18 (FIG. 17).

The locating bodies 20 are positioned with their upper side against an adjacent vertebral body and therefore form the locating elements 6.

Figure 18:
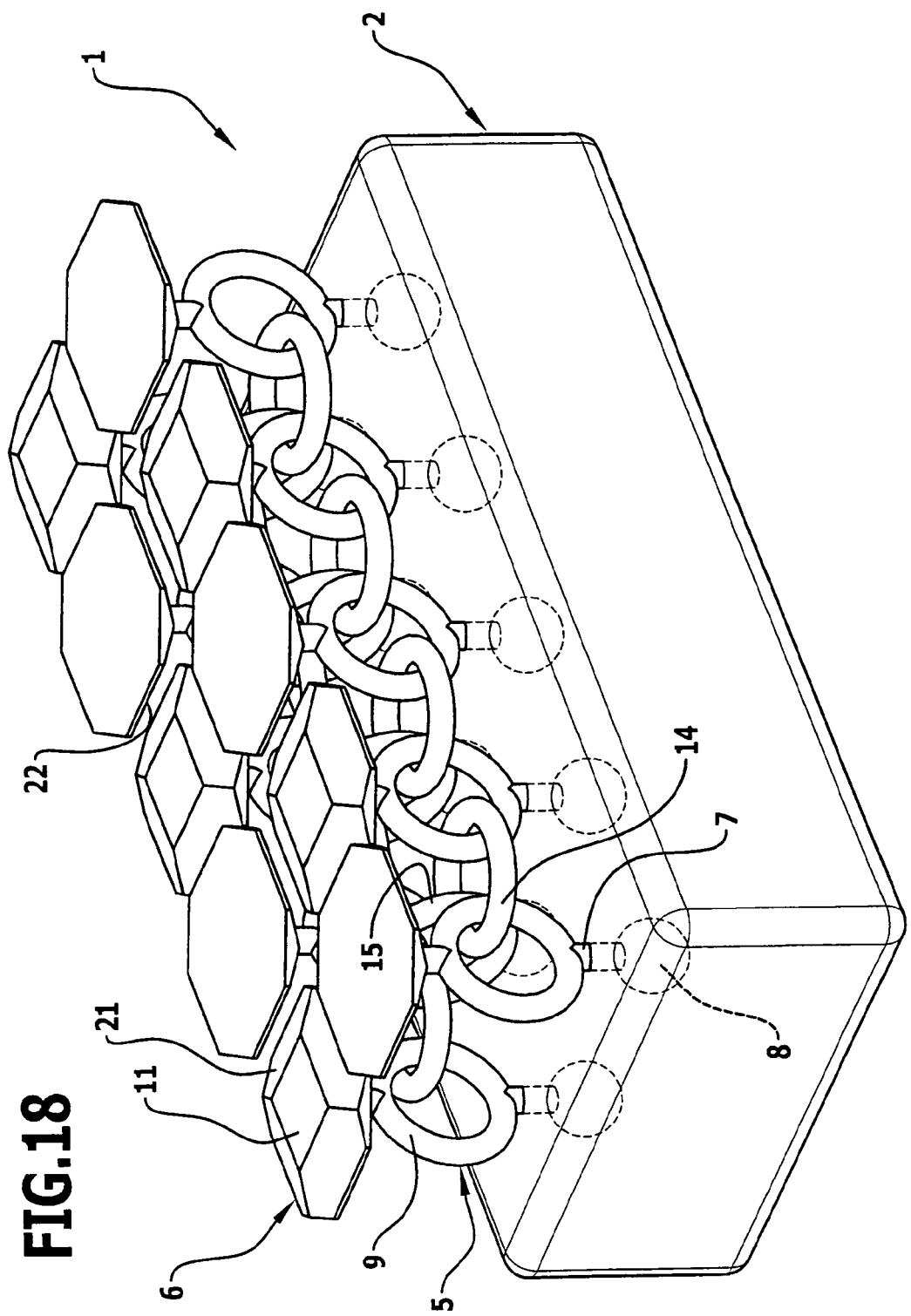
FIG. 18: is a view of an intervertebral implant similar to FIG. 10 with mutually overlapping locating elements.
Figure 19:
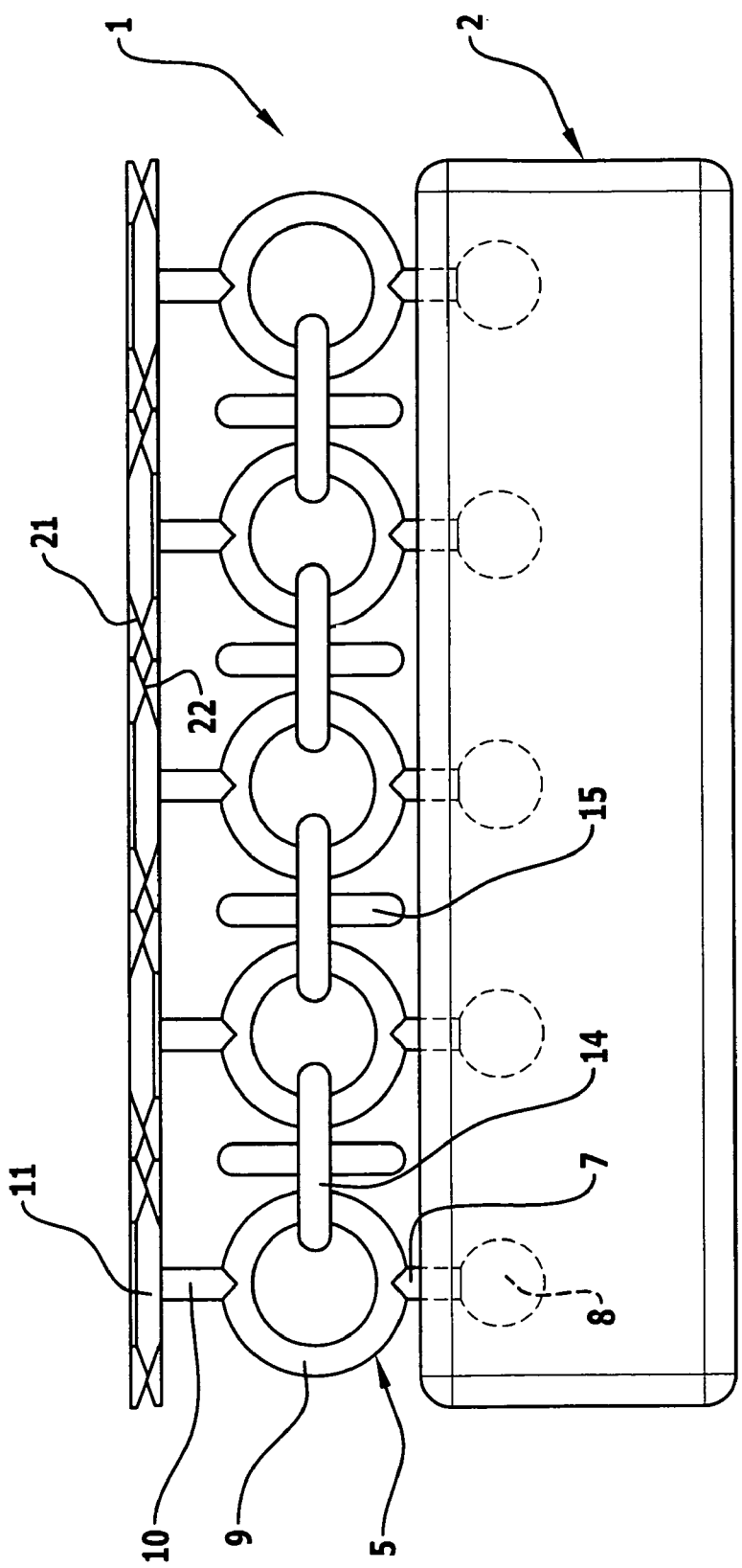
FIG. 19: is a side view of the intervertebral implant of FIG. 18.
Figure 20:
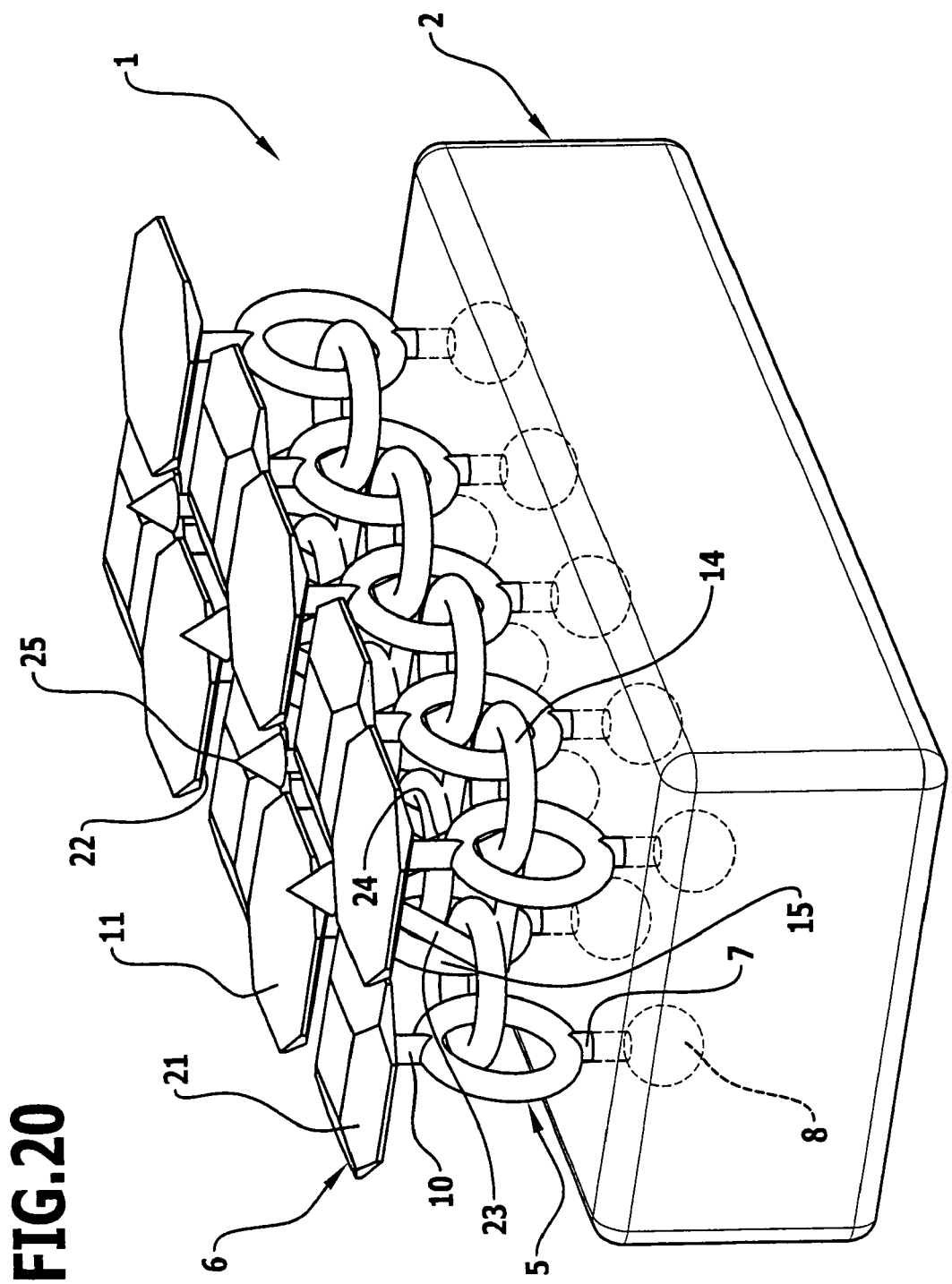
FIG. 20: is a perspective view of an intervertebral implant similar to FIG. 18 with fixing projections raised above the vertebral-body locating face.
Figure 21:
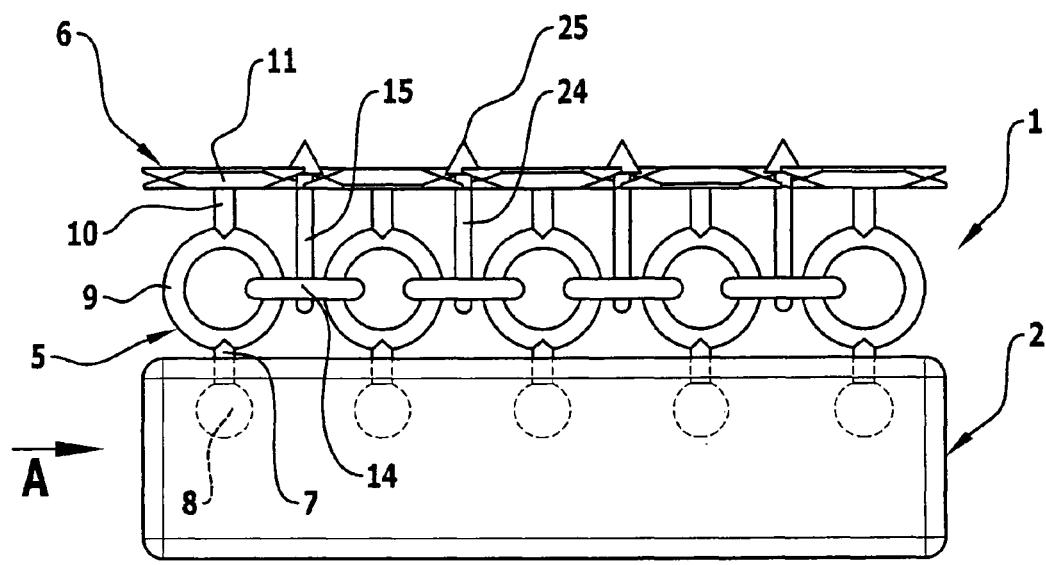
FIG. 21: is a side view of the intervertebral implant of FIG. 20.
Figure 22:
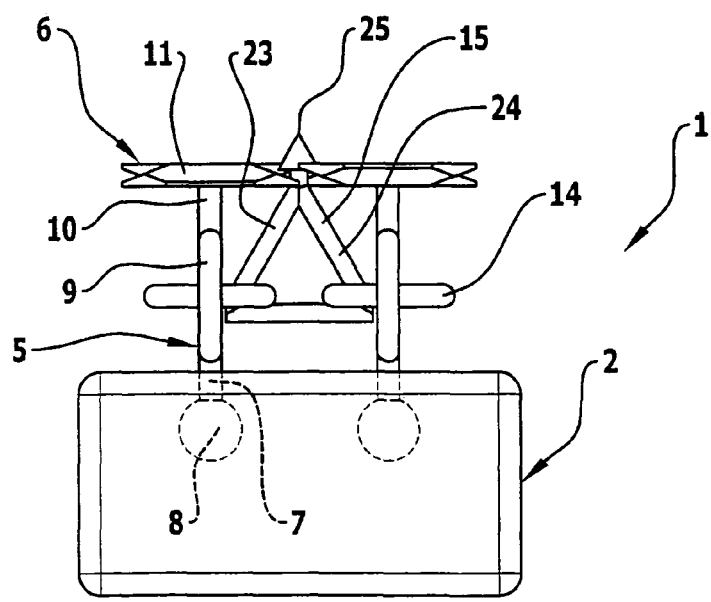
FIG. 22: is a side view of the intervertebral implant of FIG. 21 in the direction of the arrow A in FIG. 21.
Figure 23:
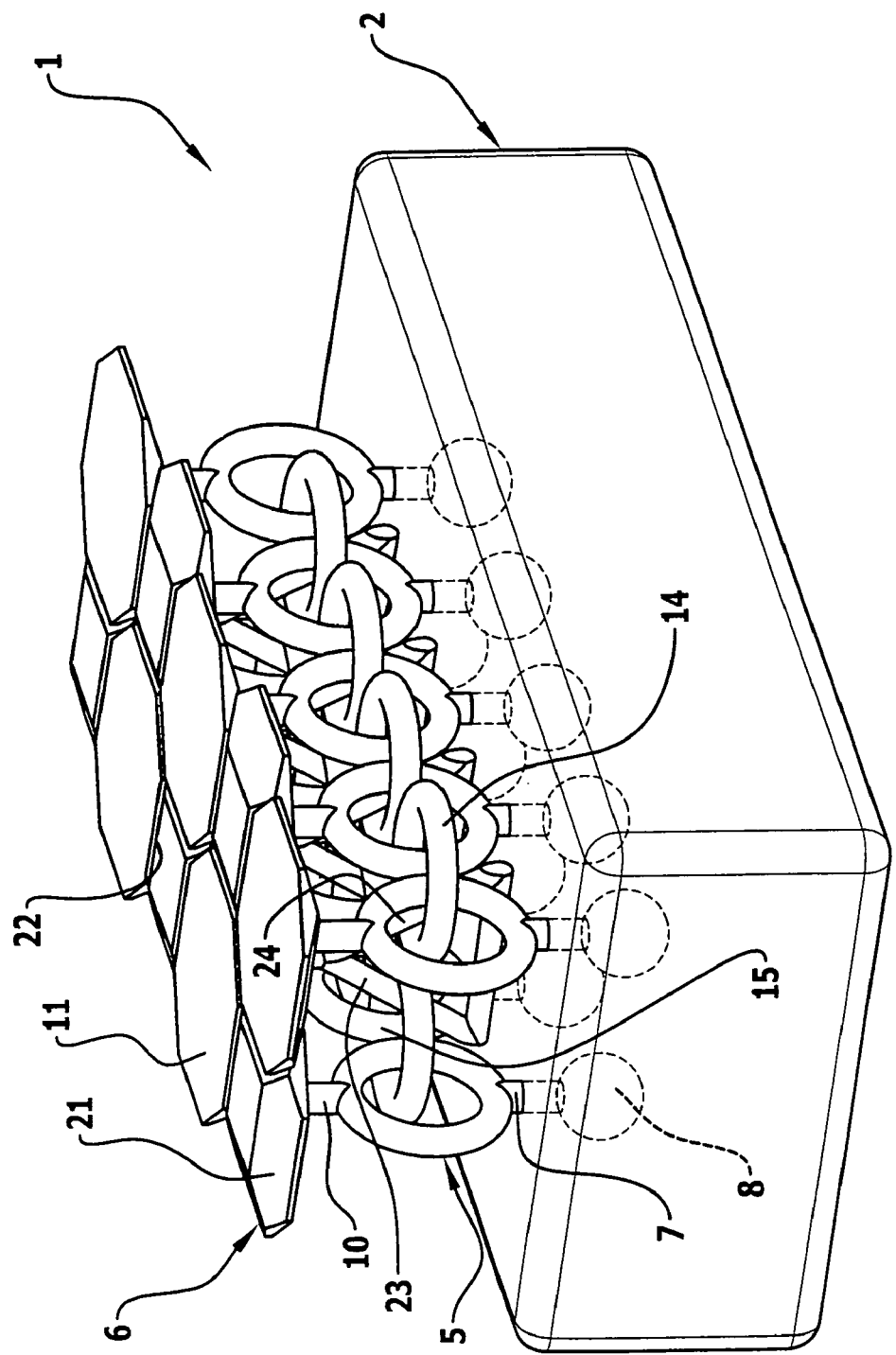
FIG. 23: is a perspective view of the intervertebral implant of FIG. 20 in the non-swollen state of the core and the retracted state of the fixing projections.
Figure 24:
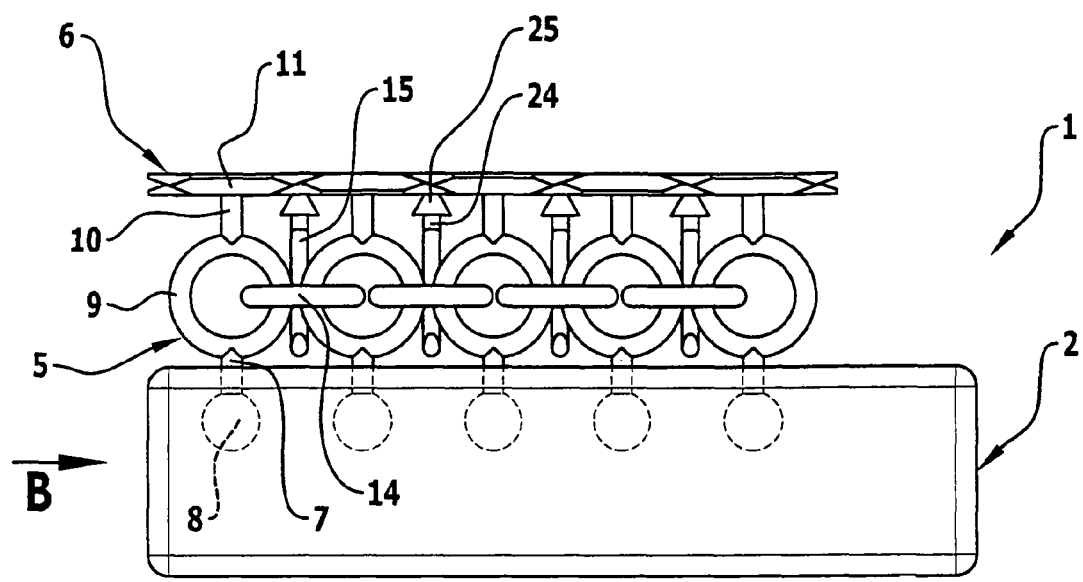
FIG. 24: is a side view of the intervertebral implant of FIG. 23.
Figure 25:
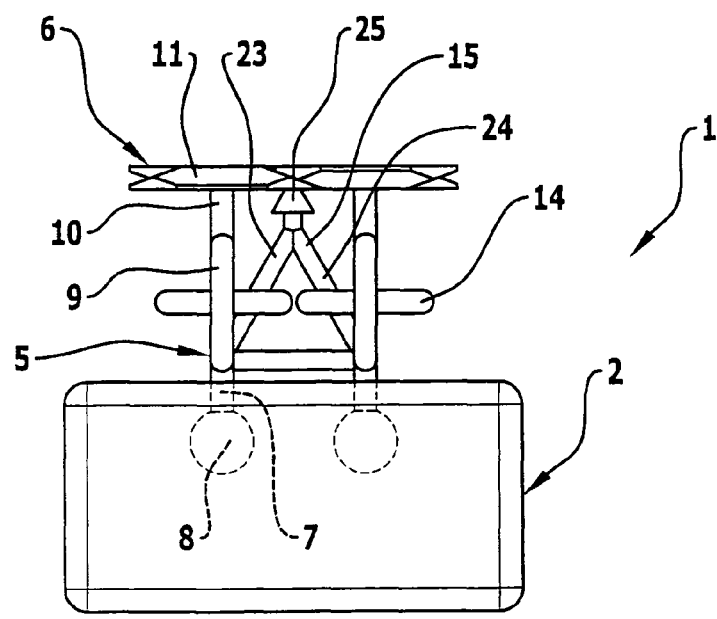
FIG. 25: is a side view of the intervertebral implant of FIG. 24 in the direction of the arrow B in FIG. 24.

The arrangement of FIGS. 18 and 19 corresponds substantially to the arrangement of FIGS. 10 and 11. Unlike the embodiment of FIGS. 10 and 11, in which the locating plates 11 in the non-swollen state of the core 2 lie closely adjacent to one another, in the embodiment of FIGS. 18 and 19 the locating plates 11 mutually overlap when the core 2 prior to absorbing liquid has not yet swollen. The edge regions 21, 22 of adjacent locating plates 11 are bevelled so that the mutually overlapping locating plates 11 slide on one another along the bevelled edge regions 21, 22. Thus, when the locating plates 11 during swelling of the core 2 move apart from one another, no gaps or only very narrow gaps are formed between adjacent locating plates 11, whereas in the previously described embodiments the width of the gaps arising correspond to the displacement movement of the support elements 5 as a result of the swelling.

In FIGS. 20 to 25 there is shown an intervertebral implant that is substantially identical in construction to that of FIGS. 18 and 19. However, in contrast to the embodiment of FIGS. 18 and 19 the limiting elements 15 disposed between adjacent rows are not annular but triangular, wherein two limbs 23, 24 of the limiting element 15 converge in the direction of the locating plates 11. The limiting elements 14 that connect adjacent support elements 5 of a row to one another pass through the triangular limiting element 15 so that, when the core 2 expands and these limiting elements 14 are pulled apart, the limiting elements 14 slide along the oblique limbs 23, 24 and therefore raise the triangular limiting element 15, i.e. displace the limiting element 15 in the direction of the locating plate 11.

At the apex the triangular limiting elements 15 carry a pointed projection 25, which remains below the locating plates 11 while the support elements 5 in the non-swollen state of the core 2 are not pulled apart from one another (FIG. 25), and which projects upwards from the locating plates 11 when the support elements 5 during the swelling of the core 2 are pulled apart from one another. These projections 25 may then penetrate into the vertebral body lying adjacent to the locating plates 11 and therefore fix the intervertebral implant 1 relative to the vertebral body.

With this construction, therefore, the increase in the volume of the core 2 is utilized on the one hand to increase the mutual spacing of the individual locating elements 6 and on the other hand to displace the triangular limiting elements 15 transversely of the plane of the locating plates 11 and therefore dig the projections 25 into the adjacent vertebra.

The described features of the various embodiments may optionally be combined and interchanged with one another, thereby producing a plurality of possible constructions, the basic principle of which is that individual support elements and locating elements may be moved independently of one another when the core 2 swells and therefore increases in size.

In all of the constructions the locating elements may be provided with a bony substance-friendly surface, thereby facilitating the growth of bony material thereon and therein. This applies in particular also to the arrangements according to FIGS. 14 to 17, in which chain-shaped elements or three-dimensional rod bodies form the locating elements. An effect achievable in these cases is that bony material grows into the open spaces of the locating elements and so a strong connection is achieved between the vertebral body on the one hand and the upper layer and hence the locating elements of the intervertebral implant 1 on the other hand.

The invention claimed is:

1. Intervertebral implant, comprising:
a core made of a swellable material, and
a vertebral-body locating face on at least one of a top and a bottom side of the implant connected to the swellable core,
the vertebral-body locating face comprising a plurality of support elements, which are respectively anchored adjacent to one another and individually in the core, and a plurality of mutually separate locating elements, which are disposed adjacent to one another and outside of the core, and
wherein the locating elements are carried by the support elements and are movable relative to one another in a plane of the vertebral-body locating face.

2. Intervertebral implant according to claim 1, wherein each of the support elements is permanently connected to a respective one of the locating elements.

3. Intervertebral implant according to claim 2, wherein each of the support elements and a respective one of the locating elements are of an integral construction.

4. Intervertebral implant according to claim 3, wherein:
the support elements are spheres which are partially embedded in the core, and
a part of the sphere projecting from the core forms a respective one of the locating elements.

5. Intervertebral implant according to claim 1 wherein the support element comprises a foot, which extends into the core with a widened portion.

6. Intervertebral implant according to claim 5, wherein the widened portion has a shape of a sphere.

7. Intervertebral implant according to claim 1, wherein the locating elements are of a plate-shaped configuration.

8. Intervertebral implant according to claim 1, wherein all of the locating elements lie in one plane.

9. Intervertebral implant according to claim 1, wherein the locating elements in a non-swollen state of the core lie adjacent to one another without an overlap.

10. Intervertebral implant according to claim 1, wherein the locating elements in a non-swollen state of the core lie adjacent to one another so as to mutually overlap in an edge region.

11. Intervertebral implant according to claim 10, wherein the locating elements are bevelled in the edge region of mutual overlap in the non-swollen state of the core.

12. Intervertebral implant according to claim 1, wherein mutually adjacent support elements and/or locating elements are connected to one another by means of a limiting element, which during the swelling of the core allows but limits a moving of the support elements and/or locating elements apart from one another.

13. Intervertebral implant according to claim 12, wherein the limiting element is of an annular configuration and in each case surrounds two mutually adjacent support elements and/or locating elements.

14. Intervertebral implant according to claim 12, wherein the support element and/or the locating element have an eye-shaped portion, through which the limiting element engages.

15. Intervertebral implant according to claim 12, wherein all of the mutually adjacent support elements and/or locating elements in a row are connected to one another by means of limiting elements.

16. Intervertebral implant according to claim 15, wherein support elements and/or locating elements from mutually adjacent rows are additionally connected to one another by means of limiting elements.

17. Intervertebral implant according to claim 1, wherein the support elements and the locating elements at sides facing one another are of an eye-shaped configuration and engage around one another in a region of the eye-shaped configuration.

18. Intervertebral implant according to claim 1, wherein the support elements and the locating elements at sides facing one another are of an eye-shaped configuration and are connected to one another in a region of the eye-shaped configuration by limiting elements so as to be movable up to a maximum distance apart from one another.

19. Intervertebral implant according to claim 17, wherein the eye-shaped region is formed by lateral faces of a three-dimensional body composed of rod-shaped edge elements.

20. Intervertebral implant according to claim 19, wherein the three-dimensional body is a cube.

21. Intervertebral implant according to claim 1, wherein:
disposed between the locating elements are fixing projections, which are displaceable transversely of the plane of the vertebral-body locating face and which are displaceable from a normal position, in which they do not project beyond the locating elements, into a fixing position, in which they project beyond the locating elements, and
for displacement of the fixing projections drive elements are provided, which can be activated by a movement of the support elements and/or the locating elements apart from one another during the swelling of the core.

22. Intervertebral implant according to claim 21, wherein the drive element comprises diverging locating faces for tension members, which are held in each case on a support element and/or locating element and, when the support elements and/or locating elements move apart from one another, slide along the locating faces in such a way that the drive element is displaced in the direction of the vertebral-body locating face.

23. Intervertebral implant according to claim 22, wherein the locating faces are formed by limbs of a triangular drive element.

24. Intervertebral implant according to claim 21, wherein the drive element comprises a limiting element that allows the support elements and/or locating elements to move up to a maximum spacing apart from one another.

* * * * *